United States Patent
Hete et al.

(10) Patent No.: US 7,431,031 B2
(45) Date of Patent: Oct. 7, 2008

(54) INSUFFLATION SYSTEM AND METHOD

(75) Inventors: Bernie F. Hete, Kittanning, PA (US); Thomas A. McCann, Monroeville, PA (US); Gardner J. Kimm, Carlsbad, CA (US)

(73) Assignee: RIC Investments, LLC, Wilmington, DE (US)

( * ) Notice: Subject to any disclaimer, the term of this patent is extended or adjusted under 35 U.S.C. 154(b) by 674 days.

(21) Appl. No.: 10/827,006

(22) Filed: Apr. 19, 2004

(65) Prior Publication Data

US 2004/0221854 A1 Nov. 11, 2004

Related U.S. Application Data

(63) Continuation-in-part of application No. 10/135,260, filed on Apr. 30, 2002, now Pat. No. 6,722,362, which is a continuation of application No. 09/596,389, filed on Jun. 16, 2000, now Pat. No. 6,439,228, which is a continuation of application No. 09/453,303, filed on Dec. 2, 1999, now Pat. No. 6,102,042.

(51) Int. Cl.
*A61M 16/00* (2006.01)

(52) U.S. Cl. ............ 128/200.26; 128/207.16; 128/207.14

(58) Field of Classification Search ............ 128/200.26, 128/207.14, 207.16, 207.15
See application file for complete search history.

(56) References Cited

U.S. PATENT DOCUMENTS

| | | | |
|---|---|---|---|
| 3,628,532 A | 12/1971 | Magrath | |
| 3,788,326 A | 1/1974 | Jacobs | |
| 4,417,573 A | 11/1983 | De Vries | |
| 4,487,155 A * | 12/1984 | Olesen | 116/70 |
| 4,488,548 A | 12/1984 | Agdanowski | |
| 4,520,812 A | 6/1985 | Freitag et al. | |
| 4,646,733 A | 3/1987 | Stroh et al. | |
| 4,825,862 A * | 5/1989 | Sato et al. | 128/207.15 |
| 5,036,847 A | 8/1991 | Boussignac et al. | |
| 5,088,486 A | 2/1992 | Jinotti | |
| 5,140,983 A | 8/1992 | Jinotti | |
| 5,186,167 A | 2/1993 | Kolobow | |
| 5,193,533 A | 3/1993 | Body et al. | |
| 5,255,675 A | 10/1993 | Kolobow | |
| 5,279,288 A | 1/1994 | Christopher | |
| 5,291,882 A | 3/1994 | Makhoul et al. | |
| 5,419,314 A | 5/1995 | Christopher | |
| 5,423,313 A * | 6/1995 | Olsson et al. | 128/204.21 |

(Continued)

OTHER PUBLICATIONS

Alexander B. Adams MPH RPT, "Tracheal Gass Insufflation (TGI)," Respiratory Care, vol. 41No. 4, 1996, pp. 285-291.

(Continued)

*Primary Examiner*—Steven O Douglas
(74) *Attorney, Agent, or Firm*—Michael W. Haas

(57) ABSTRACT

An insufflation system that includes a first tube that inserts into a patient's airway for providing a primary flow of breathing gas to such a patient. At least one insufflation catheter is provided in or within the first tube for delivering a flow of insufflation gas to the patient. In one embodiment, a flow control system is coupled between the first tube, the insufflation catheter, and a source of insufflation gas to control the flow of gas between the patient circuit, the insufflation catheter, and the source of insufflation gas. In another embodiment, a ventilator and tracheal gas insufflation system are provided in a common housing.

18 Claims, 14 Drawing Sheets

U.S. PATENT DOCUMENTS

| | | |
|---|---|---|
| 5,515,844 A | 5/1996 | Christopher |
| 5,538,002 A | 7/1996 | Boussignac et al. |
| 5,544,648 A | 8/1996 | Fischer, Jr. |
| 5,605,149 A | 2/1997 | Warters |
| 5,606,968 A | 3/1997 | Mang |
| 5,626,131 A | 5/1997 | Chua et al. |
| 5,687,714 A | 11/1997 | Kolobow et al. |
| 5,730,123 A | 3/1998 | Lorenzen et al. |
| 5,740,796 A | 4/1998 | Skog |
| 5,752,506 A * | 5/1998 | Richardson ............ 128/204.18 |
| 5,788,680 A | 8/1998 | Linder |
| 6,102,042 A | 8/2000 | Hete et al. |

OTHER PUBLICATIONS

John J. Marini et al., "Physiological Basis of Ventilatory Support," Library of CongressCatagloging-in-Publication Data, 1998, pp. 1021-1045.

John J. Marini, "Tracheal GasInsufflation: A Useful Adjunct to Ventilation ?", Thorax, vol. 491994, pp. 735-737.

G. Nakos et al., "Tracheal Gas Insufflation Reduces the Tidal Volume White PaCo2 isMaintained Constant," Intensive Care Med., vol. 20, 1994, pp. 407-413.

Sue A. Ravenscraft MD, Tracheal Gas Insufflation: Adjunct to Conventional MechanicalVentilation,: Respiratory Care, vol. 41 No. 2, 1996, pp. 105-111.

* cited by examiner

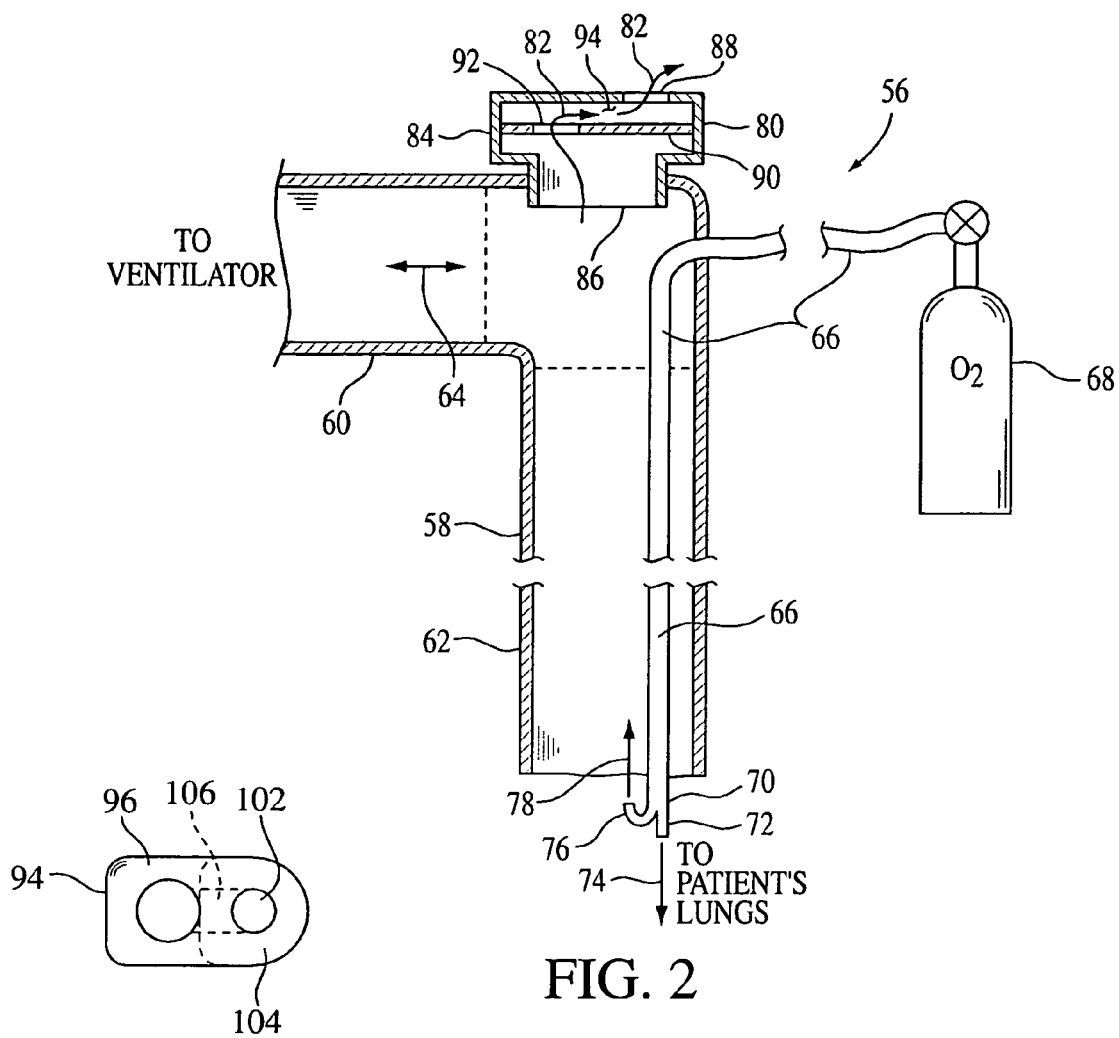
FIG. 2
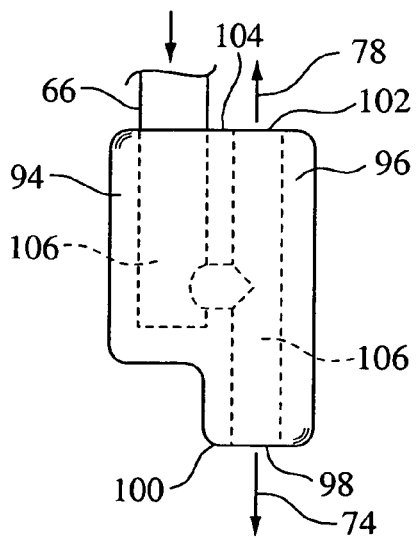
FIG. 3B
FIG. 3A
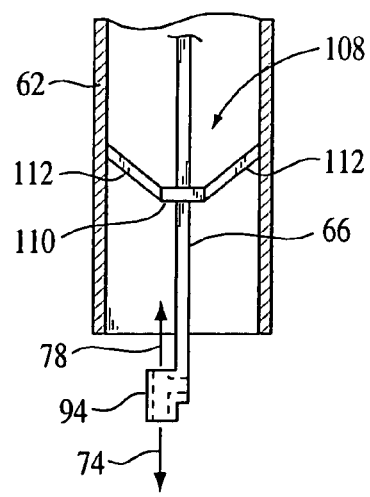
FIG. 4

INSUFFLATION SYSTEM AND METHOD

CROSS-REFERENCE TO RELATED APPLICATIONS

This application is a Continuation-In-Part and claims priority under 35 U.S.C. § 120 from U.S. patent application Ser. No. 10/135,260 filed Apr. 20, 2003, now U.S. Pat. No. 6,772,382, which is a Continuation of U.S. patent application Ser. No. 09/596,389 filed Jun. 16, 2000, now U.S. Pat. No. 6,439,228, which is a Continuation of U.S. patent application Ser. No. 09/453,303, filed Dec. 2, 1999, now U.S. Pat. No. 6,102,042, which claims priority under 35 U.S.C. § 119(e) from U.S. provisional patent application No. 60/113,222 filed Dec. 22, 1998 and 60/138,491 filed Jun. 10, 1999.

BACKGROUND OF THE INVENTION

1. Field of the Invention

The present invention pertains to an insufflation system and method that delivers a flow of insufflation gas to the airway of a patient to remove expired gases from a patient's anatomical dead space and/or the structural dead space in a breathing circuit during ventilation, and, in particular, to an insufflation system and method that delivers a flow of insufflation gas to the patient's airway in such a manner so as to minimize stagnation pressure in the patient's lungs due to the flow of insufflation gas into the patient and to an insufflation system and method that can be used in conjunction with a conventional ventilation system without altering the operation of the conventional ventilation system.

2. Description of the Related Art

It is known to reduce rebreathing of exhaled gases in an intubated patient or in a patient with a tracheostomy by providing a flow of insufflation gas, such as oxygen, an oxygen mixture, or other therapeutic gas, into the distal end of the patient's breathing circuit. FIG. 1 illustrates an example of such a conventional system, commonly referred to as a tracheal gas insufflation (TGI) system, in which a flow of insufflation gas is delivered to the airway of the patient. A primary flow of breathing gas that augments or completely supports the patient's breathing is delivered using a conventional ventilator.

As shown in FIG. 1, an endotracheal tube 30 inserted into an airway 32 of a patient 34 through the oral cavity delivers the primary flow of breathing gas from a ventilator 36 to the patient's lungs 38. In such a conventional ventilation system, a breathing circuit 40 delivers the primary flow of breathing gas from the ventilator to the patient via a first limb 42, and exhaled gas from the patient is removed via a second limb 44. First and second limbs 42 and 44 are typically flexible tubes coupled to endotracheal tube 30 via a coupling member, such as a Y-adapter. For purposes of this invention, the breathing circuit includes all of the structures associated with the ventilation system that communicate the primary flow of breathing gas with the airway of the patient, such as first limb 42, second limb 44, endotracheal tube 30 and any coupling members.

As the patient inspires, the primary flow of breathing gas is delivered by ventilator 36 to the patient's respiratory system, i.e., the airway and lungs, via breathing circuit 40. Typically, the primary flow of gas delivered to the patient by the ventilator is controlled based on the total volume delivered, the pressure of the gas delivered, or the patient's respiratory effort, the latter of which is known as proportional assist ventilation (PAV). While an endotracheal tube, which is passed into the patient's airway via the oral cavity, is illustrated in FIG. 1 as being part of the breathing circuit, it is to be understood that other methods for delivering and/or interfacing breathing gas to the patient, such as a tracheostomy tube, nasal and/or oral mask, or an nasal intubated endotracheal tube, are commonly used in conventional ventilation systems as part of the breathing circuit.

As the patient expires, i.e., breathes out, the exhaled gas, which is laden with $CO_2$, is removed from the lungs and airway via endotracheal tube 30 and second limb 44 of breathing circuit 40. Typically, an exhaust valve (not shown) associated with second limb 44 and operating under the control of ventilator 36 manages the flow of exhaust gas from the patient so that, if desired, a certain level of positive end-expiratory pressure (PEEP) can be maintained in the patient's respiratory system. In some ventilation systems, the second limb includes an exhaust valve that is controlled by the ventilator but is not contained within the ventilator itself.

It can be appreciated that at the end of exhalation, not all of the exhaled gas containing $CO_2$, for example, is exhausted to atmosphere. A certain amount of exhaled gas remains in the physiological and anatomical dead space within the patient and in the structural dead space within the breathing circuit. The structural dead space in the breathing circuit is the portion of the breathing circuit beginning at a distal end 55 of endotracheal tube 30 or tracheostomy tube to a location 46, where the exhalation (second) limb 44 separates from the rest of the breathing circuit. It is generally desirable to prevent the exhaled, $CO_2$ laden gas in this dead space from being rebreathed by the patient, so that the patient receives the maximum amount of oxygen or other therapeutic gas and a minimal amount of $CO_2$ during each breath. In some patients, such as patients with cranial injuries, it is imperative that their $CO_2$ level not be elevated.

Tracheal gas insufflation (TGI) is one method that attempts to remove the exhaled gas from the physiological, anatomical and structural dead spaces in a patient being treated with a ventilator. Tracheal gas insufflation involves introducing an insufflation gas, such as oxygen, an oxygen mixture, or other therapeutic gas, into the patient's airway 32 at the distal end of breathing circuit 40. In the embodiment illustrated in FIG. 1, an insufflation gas source 48, such as a pressurized tank or oxygen or an oxygen wall supply, delivers a flow of insufflation gas via a conduit 50 as a stream of gas into the patient's airway. Conduit 50 is also referred to as an "insufflation catheter." In a conventional TGI system, a proximal end of conduit 50 is coupled to insufflation gas source 48 through a control valve 52, and a distal end of conduit 50 is located generally within or near the distal end of endotracheal tube 30 so that the flow of insufflation gas is directed toward lungs 38, as indicated by arrow 54. Typically, the distal end of conduit 50 is located just above the patient's carina. The oxygen rich flow of insufflation gas discharged from the distal end of conduit 50 displaces the exhaled air in the anatomical and structural dead spaces so that the patient inhales the fresh (non $CO_2$ laden) gas on the next breath, thereby minimizing rebreathing of $CO_2$ to keep the patient's $CO_2$ levels as low a possible.

Conventionally, there are two techniques for delivering the flow of tracheal insufflation gas to a patient. According to a first TGI technique, the flow of insufflation gas is delivered to the patient continuously during the entire breathing cycle while the ventilator delivers the primary flow of breathing gas to the patient. This technique is commonly referred to as a "continuous TGI system." This continuous TGI delivery method, however, has a significant drawback in that conventional ventilators are not capable of accounting for the additional volume of gas delivered to the patient by the continuous TGI system. As a result, the extra volume of gas bled into the breathing circuit by the continuous TGI system is simply summed with the prescribed volume of gas being delivered by the ventilator. A possible outcome is that an excessive pressure of gas is delivered to the patient, possibly over-inflating the patient's lungs. This excessive pressure is referred to as "autoPEEP." A disadvantage associated with autoPEEP is that it increases the patient's work of breathing, because in order to initiate inspiration, the patient must generate an inhalation force that is strong enough to overcome the autoPEEP pressure. AutoPEEP may also cause tissue damage due to the hyper-inflation of the patient's lungs.

These problems are dealt with, at least in part, in conventional continuous TGI systems by carefully adjusting the ventilator settings to avoid over-inflation. It can be appreciated that "fooling" the ventilator so that the continuous flow of insufflation gas does not over-inflate the patient's respiratory system is not an ideal solution because it does not maximize the operating abilities of the ventilator. The ventilator must be specifically configured to deal with this extra insufflation gas, rather than being configured as it normally would in the absence of the flow of insufflation gas. On the other hand, maximizing the operating characteristics of the ventilator by setting it up without accounting for the flow of insufflation gas may result in excessive $CO_2$ levels in the patient or hyperinflation of the patient. In addition, adjusting the operating characteristics of the ventilator to prevent over-inflation when a continuous TGI system is used requires a highly trained operator to make the correct fine-tuning adjustments to the ventilator. Furthermore, this continuous TGI technique requires constant monitoring of the patient and ventilator system because changes in the patient's breathing cycle that may require reconfiguring of the ventilator or the continuous TGI system can occur in very short time periods.

According to a second TGI technique, referred to as a "phasic TGI system," the flow of insufflation gas is controlled so that the insufflation flow is only delivered to the patient during the expiratory phase, preferably at the end, while the exhaust valve associated with the second limb of the breathing circuit is open. Because the exhaust valve is open when the flow of insufflation gas is delivered, the extra volume of insufflation gas being delivered to the patient displaces an equal volume of gas out of the breathing circuit through the exhaust port and, therefore, does not over-inflate the patient's lungs. This phasic approach, however, requires a relatively complicated control mechanism for controlling the flow of insufflation gas in conduit 50, for example, by controlling valve 52 using ventilator 36, to ensure that the flow of insufflation gas is only delivered while the exhaust valve associated with second limb 44 is open. It can be appreciated that this phasic TGI technique increases the complexity and cost of the ventilation system and the TGI system due to the precise timing required to control the operation of the ventilator and valve 52, so that the gas is delivered at the correct time during the patient's breathing cycle.

Another drawback associated with conventional TGI systems, including both the continuous and phasic TGI techniques, is that autoPEEP is also caused by a phenomenon known as stagnation pressure. Stagnation pressure, also known as dynamic pressure, is the pressure or force generated when a flowing gas is brought to rest by isentropic flow against a pressure gradient. The magnitude of the stagnation pressure is proportional to the square of the change in velocity of the gas. Because the insufflation gas in a conventional TGI system is directed into the patient's airway using a relatively small diameter tubing, typically 0.1 inch diameter, it has a relatively high velocity, which is decelerated into a closed volume, namely the patient's airway and lungs. As a result, a stagnation pressure is created within the patient, thereby exacerbating the autoPEEP problem. It should be noted that the problem of autoPEEP due to stagnation pressure is prevalent in both the continuous and phasic TGI systems because the timing at which the flow of insufflation gas is introduced into the patient does not affect the magnitude of the stagnation pressure generated.

SUMMARY OF THE INVENTION

Accordingly, it is an object of the present invention to provide a tracheal gas insufflation system for introducing a flow of insufflation gas into the airway of a patient that overcomes the shortcomings of conventional TGI techniques. This object is achieved according to one embodiment of the present invention by providing a TGI system that includes an insufflation catheter having a proximal end portion that is located generally outside a patient and a distal end portion that is located in an airway of a patient during use. The insufflation catheter provides the flow of insufflation gas to the patient. A flow control system is coupled between the patient circuit, the insufflation catheter, and a source of insufflation gas to control a flow of gas between the patient circuit, the insufflation catheter, and the source of insufflation gas. This flow control system allows the user to control the deliver of insufflation gas via the insufflation catheter in an easy and efficient manner.

In one embodiment of the present invention, the insufflation catheter includes a vent assembly at the distal end portion of the insufflation catheter. The vent assembly has first and a second port that discharges the flow of insufflation gas from the insufflation catheter. It can be appreciated that a vector force will be associated with the discharge of the flow of insufflation gas from each port of the vent assembly.

In this embodiment, a first port in the vent assembly directs a first portion of the flow of insufflation gas from the insufflation catheter generally in a first direction into the patient's respiratory system. In addition, a second port directs a second portion of the flow of insufflation gas generally in a second direction out of the patient's respiratory system. The vent assembly is configured and arranged such that a net of all second vector force components associated with the flow of insufflation gas in the second direction is greater than a net of all first vector force components in the first direction responsive to the flow of insufflation gas exiting the venting means. As in a conventional TGI system, providing the flow of insufflation gas in the first direction generates a positive stagnation pressure. However, providing the flow of insufflation gas in the second direction generates a negative stagnation pressure within the patient. The present inventors discovered that a pressure drop occurs in the patient or in the patient circuit as a result of the insufflation catheter being placed in the patient, which tends to increase the positive stagnation pressure. Therefore, the flow of insufflation gas in the second direction should be increased above that in the first direction to counteract the pressure drop in the patient circuit. This ensures that the negative stagnation pressure offsets out the positive stagnation pressure, so that substantially no stagnation pressure or autoPEEP is generated within the patient.

The present invention also contemplates directing the flow of insufflation gas from the insufflation catheter in a variety of directions and locating the distal end of the insufflation catheter in a variety of locations, so long as the net vector force of the expelled gas from the vent assembly is sufficiently low so as to avoid creating a problematic stagnation pressure in the patient.

In another embodiment of the present invention, instead of the vent assembly with two ports, two insufflation catheters are provided to accomplish the same function. The distal end of a first insufflation catheter directs the flow of insufflation gas in the first direction generally toward the patient's lung. The flow in the second direction, generally opposite the first direction to provide a balancing of the positive and negative pressures created by the flow of insufflation gas, is provided by a second insufflation catheter. Of course, this balancing of pressures may require providing a larger flow of insufflation gas in the second direction to overcome the pressure drop induced by the presence of the insufflation catheter or catheters in patient. The distal end of the second insufflation catheter is configured and arranged such that, in an operative position, it directs the flow of insufflation gas in the second direction, away from the lungs. The flow of gas in the first and second insufflation catheters is provided substantially the same so that the combination of flows from these catheters performs the same function as the bi-directional vent discussed above, i.e., the net vector forces resulting from the introduction of insufflation gas into the patient's airway at the distal end of the first and second insufflation catheter combination is substantially zero, thereby minimizing the creation of a stagnation pressure or autoPEEP in the patient.

It is a further object of the present invention to provide an insufflation system that does not create significant positive stagnation pressures within the patient and that can be used in a conventional ventilation system to provide a flow of insufflation gas into the patient's airway. This object is achieved by providing an insufflation system as described above and that further includes an exhaust valve disposed at a portion of the breathing circuit outside the patient. The exhaust valve is configured and arranged to exhaust gas from the breathing circuit to ambient atmosphere at an exhaust flow rate that that is substantially the same as the flow rate at which the insufflation gas is introduced into the breathing circuit by the TGI system. The flow of insufflation gas into the patient and discharge of exhaust gas to ambient atmosphere are provided irrespective of the primary flow of breathing gas to the. The result of this balance between the amount of gas introduced to the breathing circuit and the amount of gas exhausted from the breathing circuit is that there is no net increase or decrease in the amount of gas in the breathing circuit. Therefore, no special modification of the ventilator or its operation is needed.

This equalization of the flow of gas into and out of the patient's breathing circuit provided by the TGI system is accomplished in one embodiment of the present invention by continuously exhausting gas from the breathing circuit over a range of pressures within the breathing circuit while the flow of insufflation gas is also continuously introduced into the patient. As a result, gas is continuously exhausted from the breathing circuit preferably at the same rate the flow of insufflation gas is introduced into that circuit.

It is yet another object of the present invention to provide a system for supplying a therapeutic gas to a patient in which a flow of insufflation gas is introduced into the patient's airway without over inflating the patient and without any modification of the operation of the gas flow generator, which provides a primary flow of breathing gas to the patient, to account for the excess gas introduced into the breathing circuit. This object is achieved by providing a system for supplying therapeutic gas to a patient that includes a first tube that inserts into a patient's airway for providing a primary flow of breathing gas to the patient. An insufflation catheter generally disposed in the first tube provides a flow of insufflation gas to the patient at a first flow rate. An exhaust valve is coupled to the first tube and is configured and arranged to exhaust gas from the first tube to ambient atmosphere at a second flow rate that is substantially the same as the first flow rate. The flow of insufflation gas into the patient and the discharge of exhaust gas to ambient atmosphere are provided irrespective of the primary flow of breathing gas to the patient. In one embodiment of the present invention, the exhaust valve continuously exhausts gas from the first tube to ambient atmosphere at the second flow rate despite pressure variations within the first tube.

It is still another object of the present invention to provide an insufflation attachment for use with a conventional ventilation system, which provides a primary flow of breathing gas to the patient. The insufflation attachment is used to introduce a flow of insufflation gas into the airway of the patient in a manner that overcomes the shortcomings of conventional insufflation techniques. According to the principles of the present invention, this object is achieved by providing an insufflation attachment that includes a first tube adapted to be coupled in a breathing circuit. The proximal end of an insufflation catheter is coupled to the first tube. The insufflation catheter is configured and arranged such that a distal end portion thereof is generally disposed in an endotracheal or tracheostomy tube when the first tube is coupled to the breathing circuit. A vent assembly is provided at the distal end of the insufflation catheter. The vent assembly has at least one port that discharges the flow of insufflation gas from the insufflation catheter. The vent assembly includes a first port that directs a first portion of the flow of insufflation gas from the insufflation catheter generally in a first direction into the patient's respiratory system. In addition, a second port directs a second portion of the flow of insufflation gas generally in a second direction out of the patient's respiratory system. The vent assembly is configured and arranged such that a net of all vector force components in the first direction and in the second direction resulting from the discharge of insufflation gas into the patient's airway via the vent assembly is substantially zero. As noted above, the positive stagnation pressure created by the flow of insufflation gas in the first direction is offset by the negative stagnation pressure created by the flow of insufflation gas in the second direction so that substantially no stagnation pressure is generated within the patient.

In an alternative embodiment, instead of the vent with two ports, two insufflation catheters are employed. The distal end of a first insufflation catheter directs the flow of insufflation gas only in the first direction toward the patient's lung, thereby simplifying the configuration for this catheter. The opposing flow in the second direction opposite the first direction is provided by a second insufflation catheter also coupled to the first tube. More specifically, the distal end of the second insufflation catheter is configured and arranged such that, in an operative position, it directs the flow of insufflation gas in the second direction, so that the net vector forces associated with the flow of insufflation gas from the first and second insufflation catheters are substantially zero or so that a greater flow is provided in the second direction to provide additional negative stagnation pressure that offsets the pressure drop induced by the presence of the insufflation catheter in the breathing circuit.

It is a further object of the present invention to provide an insufflation attachment that avoids autoPEEP due to a stagnation pressure and that can be used in a conventional ventilation system in which a flow of insufflation gas is continuously introduced into the patient's airway. This object is achieved by providing an insufflation attachment as described in either of the immediately preceding paragraphs and further comprising an exhaust valve coupled to the first tube. The exhaust valve is configured and arranged to exhaust gas from the first tube, i.e., the breathing circuit, such that the flow rate for the exhaust gas exiting the breathing circuit is substantially the same as the flow rate for the insufflation gas introduced into the breathing circuit by the TGI system. The flow of insufflation gas into the patient and the discharge of exhaust gas to ambient atmosphere are provided irrespective of the primary flow of breathing gas to the patient. The result of this balance between the amount of gas introduced to the breathing circuit and the amount of gas exhausted from the breathing circuit irrespective of the primary flow of breathing is that there is no net increase or decrease in the amount of gas in the breathing circuit. Therefore, the ventilator does not "see" the introduction of the insufflation gas into the breathing circuit so that no special modification of the ventilator or its operation are needed. In one embodiment of the present invention, exhausting gas from the breathing circuit is done continuously over a range of pressures within the breathing circuit at a flow rate that matches the flow rate of the insufflation gas. As a result, there is substantially no net accumulation of gas in the breathing circuit due to the introduction of insufflation gas into the breathing circuit.

It is yet another object of the present invention to provide an insufflation method that overcomes the shortcomings of conventional TGI techniques. This object is achieved by providing a TGI method that includes providing a patient circuit adapted to couple a ventilator to an airway of a patient and an insufflation catheter having a proximal end portion located generally outside a patient and a distal end portion adapted to be located in an airway of a patient for providing a flow of insufflation gas to such a patient. The method also includes providing a source of insufflation gas and controlling a flow of gas between the patient circuit, the insufflation catheter, and the source of insufflation gas.

In a further embodiment, the flow of insufflation gas is directed from the insufflation catheter such that a net of all vector force components in a first direction generally into the patient's respiratory system and in a second direction generally out of the patient's respiratory system resulting from discharging the insufflation gas into the patient's airway is substantially zero. In one embodiment, this is accomplished by directing a first portion of the flow on insufflation gas in a first direction generally toward the patient's lungs and directing a second portion in a second direction generally opposite the first direction to minimize or eliminate the generation of stagnation pressure in the patient. As noted above, the present invention also contemplates providing a greater flow of gas in the second direction than is provided in the first direction to overcome the additional pressure drop imposed by the presence of the insufflation catheter in the system.

It is a further object of the present invention to provide an insufflation method that overcomes the shortcomings of conventional insufflation techniques in which a flow of insufflation gas is delivered to the airway of patient in addition to the primary flow of breathing gas. This object is achieved by providing a method that includes the steps of (1) delivering the primary flow of breathing gas to the airway of the patient via a breathing circuit, (2) delivering a flow of insufflation gas to the airway of a patient at a first flow rate, and (3) exhausting gas from the breathing circuit to ambient atmosphere at a second flow rate that is substantially the same as the first flow rate. The flow of insufflation gas into the patient and the discharge of exhaust gas to ambient atmosphere are provided irrespective of the primary flow of breathing gas to the patient. In a further embodiment of the present invention, the exhaust valve continuously exhausts gas from the breathing circuit to ambient atmosphere at the second flow rate over a range of pressures within the breathing circuit.

It is a still further object of the present invention to provide a ventilator and tracheal gas insufflation system. This combined system includes a patient ventilation system adapted to generate a flow of gas for delivery to an airway of a patient and a patient circuit operatively coupled to the ventilation system for carrying the flow of gas from the ventilation system to an airway of a patient. The combined system also includes an insufflation system adapted to generate a flow of insufflation gas for delivery to an airway of such a patient, and an insufflation catheter operatively coupled to the insufflation system for carrying the flow of gas from the insufflation system to an airway of a patient, wherein a portion of the insufflation system is disposed within the patient circuit. A single housing contains both the patient ventilation system and the insufflation system.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIG. 2 is a sectional view of a portion of a breathing circuit illustrating the insufflation system of the present invention;

FIGS. 3A and 3B are side and top views, respectively, illustrating one embodiment of a bi-directional vent for directing the flow of insufflation from the insufflation catheter;

FIG. 4 is a sectional view of a portion of the insulation system illustrating a further embodiment of the present invention;

DETAILED DESCRIPTION OF THE PRESENTLY PREFERRED EMBODIMENTS OF THE INVENTION

Figure 1:
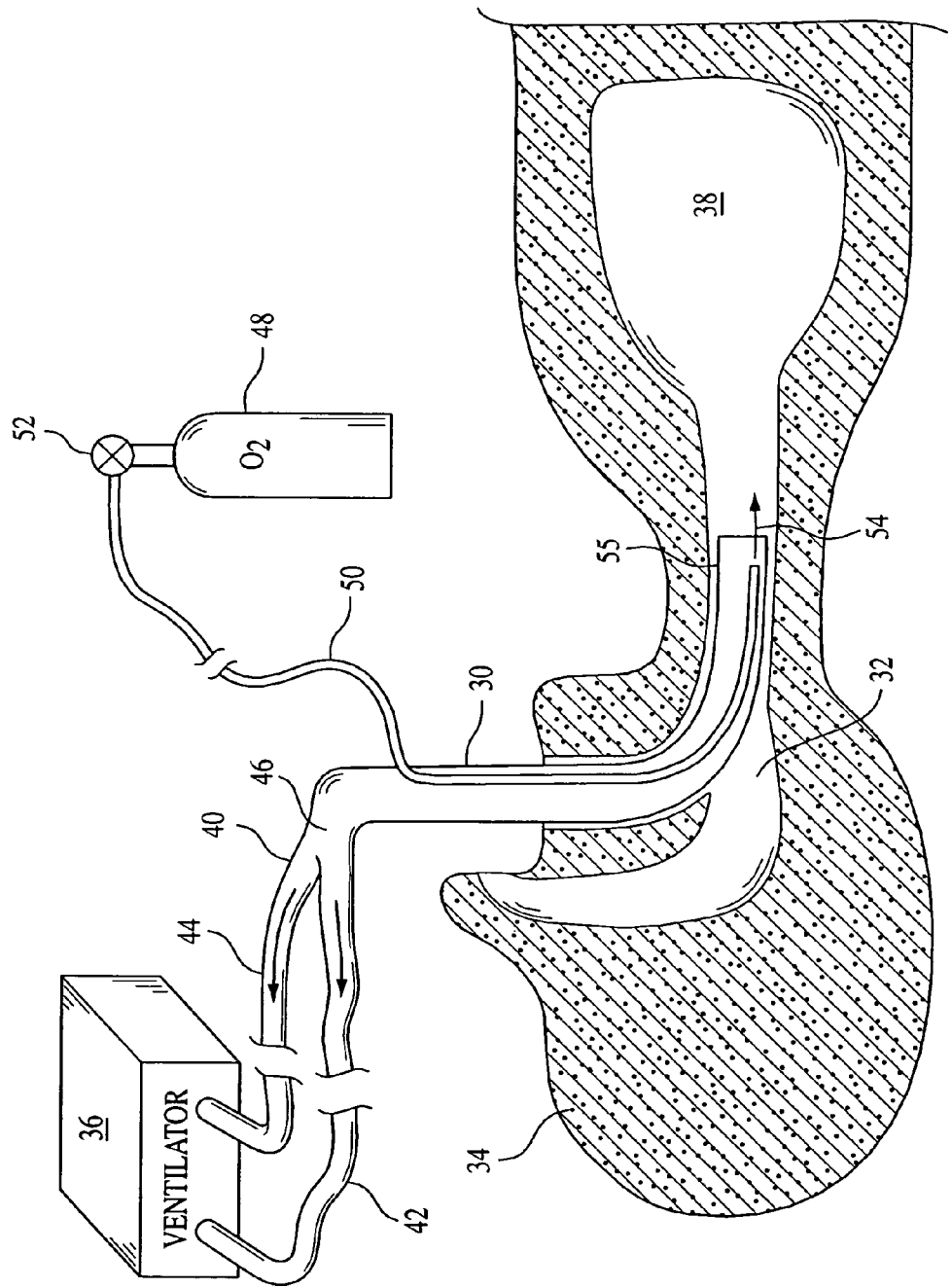
FIG. 1 is a sectional view illustrating a patient coupled to a ventilator and a conventional tracheal gas insufflation system.
Figure 5A:
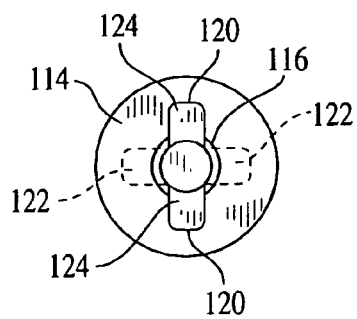
FIGS. 5A-5C are top, side and bottom views, respectively, illustrating another embodiment of a bi-directional vent for directing the flow of insulation gas in opposite directions from the distal end of the insulation catheter.
Figure 5B:
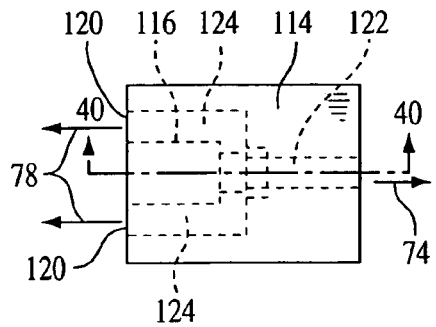
Figure 5C:
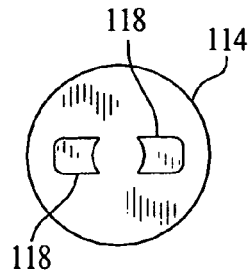
Figure 5D:
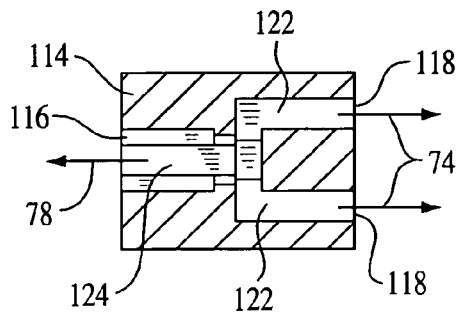
FIG. 5D is a sectional view taken along line 5D-5D in FIG. 5B.

FIG. 2 illustrates a first embodiment of an insufflation system 56 according to the principles of the present invention. For the sake of simplicity, FIG. 2 illustrates a portion of the breathing circuit that couples the patient with a ventilator, including a distal portion for the breathing circuit, generally indicated at 58, that inserts into the patient's airway and a proximal portion, generally indicated at 60, that remains outside the patient and is coupled to a ventilator (not shown) via a flexible tube or tubes as described above with reference to FIG. 1.

A first tube 62, which is a conventional endotracheal tube or tracheostomy tube, inserts into the patient's airway and attaches to a conventional ventilator breathing circuit for providing a primary flow of breathing gas, generally indicated by arrow 64, to the patient. As with conventional TGI systems, insufflation system 56 of the present invention includes a second tube 66, which, as noted above, is referred to as an "insufflation catheter," that provides a flow of insufflation gas to the airway of the patient from a source 68 of such gas. Preferably insufflation catheter 66 is much smaller in diameter than first tube 62 to minimize the resistance to the primary gas flow caused by the insufflation catheter. This additional resistance increases the pressure drop in the first tube that can add to the positive stagnation pressure experienced by the patient.

In the illustrated embodiment, insufflation catheter 66 is only coupled to first tube 66 where the insufflation catheter passes through the wall of first tube 62. However, the present invention contemplates that the insufflation catheter can be secured to or integral with the wall of first tube 62. For example, a portion of the insufflation catheter or the entire length of the insufflation catheter can be formed within the wall the first tube, which reduces the amount of material within first tube 62 and, hence, flow resistance, thereby maximizing the efficiency of the primary gas flow through the first tube. Source 68, which provides the flow of insufflation gas, such as oxygen, an oxygen mixture, or a therapeutic gas, can be any suitable device, such as a pressurized tank of gas, an oxygen concentrator, or a piped wall supply typically found in hospitals.

In the embodiment shown in FIG. 2, a proximal end of insufflation catheter 66 is coupled to source 68 of insufflation gas and a distal end portion is generally located near the distal end portion of first tube 62. Typically, the distal end of insufflation catheter 66 is located just above the patient's carina and remains within first tube 62 or extends therebeyond. A vent assembly 70 is provided at the distal end of insufflation catheter 66 to control the discharge of insufflation gas into the patient from the distal end of insufflation catheter 66. More specifically, vent assembly 70 is configured and arranged such that a cancellation or balancing of vector forces associated with the injection of the flow of insufflation gas from the distal end of insulation catheter 66 takes place. That is, the net of all vector force components in a first direction generally into the patient's respiratory system (down in FIG. 2) and in a second direction generally out of the patient's respiratory system (up in FIG. 2) resulting from the discharge of the flow of insufflation gas into the patient's airway by the vent assembly is substantially zero. As a result, substantially no stagnation pressure is generated in the patient as a result of delivering the insulation gas into the patient's airway.

The present inventors discovered that a positive stagnation pressure is generated in the patient relative to the desired PEEP level when the vector sum of all gas discharged generally toward the lungs is greater than the vector sum of all gas discharged generally away from the lung. Similarly, a negative stagnation pressure is generated in the patient relative to the desired PEEP level when the vector sum of all gas discharged generally away the lungs is greater than the vector sum of all gas discharged generally toward from the lung. The present invention further proposed solving the problem of increased positive stagnation pressures that occur with conventional TGI techniques by configuring vent assembly 70 so that a balancing of the vector sum of these gas streams, and, hence, a balancing of the positive stagnation pressure and the negative stagnation pressure generated by these gas streams, takes place. That is, the net or total of the vector sum of all gas discharged generally toward the lungs and the vector sum of all gas discharged generally away from the lung is substantially zero so that the generated positive stagnation pressure is offset by a substantially equal negative stagnation pressure.

The present inventors also recognized that the presence of the insufflation catheter in tube 62 can cause a pressure drop in this tube where the catheter is located. As a result, if the flow in the first direction 74 is exactly equal to the flow in the second direction 78, a positive stagnation pressure may still be created. That is, the presence of the insufflation catheter in tube 62, i.e., the flow restriction imposed by the presence of the insulation catheter in tube 62, prevents the negative stagnation pressure caused by the flow in the second direction from offsetting the positive stagnation pressure caused by the flow in the first direction when the flow in the first and second directions are equal. To address this possibility, the present invention contemplates making the flow the in the section direction 78 larger than the flow in the first direction 74 so that an additional amount of negative stagnation pressure is created to account for the pressure drop in tube 62 caused by the presence of the insufflation catheter. As a result, no significant positive stagnation pressure is generated in the patient.

In the embodiment illustrated in FIG. 2, balancing of the negative stagnation pressure (NEEP) and PEEP is accomplished by providing a bi-directional vent 70 at the distal end of insulation catheter 66 that directs the flow of insufflation gas in two opposite directions. More specifically, a first section 72 directs a first portion of the flow of insulation gas, indicated by arrow 74, in a first direction generally toward the patient's lungs. A second section 76 directs a first portion of the flow of insufflation gas, indicated by arrow 78, in a second direction generally opposite the first direction. As with a conventional TGI system, directing a first portion of the flow of insulation gas in first direction 74 creates a positive stagnation pressure within the patient relative to the desired PEEP level. However, this positive stagnation pressure is offset by directing a second portion of the flow of insufflation gas in second direction 78, which creates a negative stagnation pressure NEEP relative to the desired PEEP level, so that no net stagnation pressure is created in the patient as a result of the TGI system of the present invention.

Preferably, the rate and amount of flow of insufflation gas in first direction 74 and second direction 78 are equal so that positive stagnation pressure caused by flow in first direction 74 is substantially cancelled or balanced out by the negative stagnation pressure caused by the flow in second direction 78. It can be appreciated, however, that the flow in first direction 74 and second direction 78 need not be exactly equal so long as the difference therebetween does not result in the generation of an unacceptable level of stagnation pressure, i.e., autoPEEP. It is also preferable that the exhaust ports in first section 72 and second section 76 are relatively close to one another to maximize the cancellation effect of the two opposite flows. It can be appreciated, however, that proximity between the ports is not a requirement for cancellation within a given tube. Thus, the exhaust ports can be spaced apart from one another over a range of distances so long as the distance between these ports does not reduce the cancellation effect below acceptable levels.

Furthermore, in the illustrated embodiment, the distal end portion of insufflation catheter 66 is positioned beyond the distal tip of first tube 62 so that both the first flow 74 and second flow 78 of insufflation gas originate outside the first tube. This is acceptable so long as the patient's tissues do not impede these flows. The present invention also contemplates, however, that one or both of the first and second flows 74 and 78 can originate within first tube 62.

The vent assembly described so far is suited for use with a conventional phasic or continuous flow TGI system. That is, the bi-directional vent can be used with either a phasic or a continuous TGI system to reduce or eliminated the stagnation pressure, i.e., autoPEEP, problem. The timing used by the phasic TGI system to ensure that the flow of insufflation gas is provided only at the end of exhalation so that over-inflation does not occur in combination with the bi-directional flow of the insufflation gas provided by the bi-directional vent assembly of the present invention minimizes the autoPEEP resulting from increased positive stagnation pressures.

However, as noted above, the phasic TGI approach remains relatively complicated and costly due to the need to control the flow of the insufflation gas in synchronization with the patient's breathing. Therefore, it is preferable to provide the insufflation system of the present invention in a continuous TGI system. Although a continuous TGI system simplifies the delivery of the insufflation gas, conventional continuous TGI systems are inefficient in their use of the ventilator in order to avoid over-inflation because they require that the operating settings of the ventilator be modified from the desired non-TGI settings.

A further embodiment of the present invention enables insufflation system 56 to be used with a continuous TGI system. This is made possible by providing an exhaust valve 80 to exhaust a flow of gas from the first tube, i.e., breathing circuit 58. In the illustrated embodiment, exhaust valve 80 is provided at a proximal end portion of first tube 62, which is at the distal end portion of the breathing circuit, to exhaust a flow of gas from the first tube. It is to be understood, however, that the exhaust valve can be provided anywhere along the exhaust limb so long as exhaust valve 80 is located outside the patient and vents gases from within the first tube, i.e., the breathing circuit, to ambient atmosphere, as generally indicated by arrows 82. The present invention contemplates that the functions of these exhaust valve described below can be incorporated into the exhaust valve in the ventilator.

Exhaust valve 80 configured and arranged to exhaust gas from the first tube (breathing circuit) such that the flow rate for exhaust gas exiting the breathing circuit is substantially the same as the flow rate for insufflation gas introduced into the breathing circuit in the patient's airway by the TGI system. As a result of this balance between the rate at which insufflation gas introduced to the breathing circuit and the amount of gas exhausted from the breathing circuit, there is no net increase or decrease in the amount of gas within the breathing circuit while the TGI system is operating. That is, there is no net change in the volume of gas in the system over a respiratory cycle as a result of the presence of the TGI system. Therefore, no special modification of the ventilator or its operation are needed. The TGI system of the present invention is considered to be "transparent" with respect to the ventilator.

In the embodiment illustrated in FIG. 2, exhausting gas from first tube 62 at substantially the same rate the flow of insulation gas enters insufflation catheter 66 is accomplished by continuously exhausting gas from the breathing circuit at a relatively constant flow rate over a range of pressures within the first tube while the flow of insufflation gas is introduced at substantially the same constant flow rate. As a result, a continuous, non-interrupted, flow of gas is exhausted from the breathing circuit generally at the same rate the flow of insulation gas is introduced into that circuit. In addition, the discharge of exhaust gas from the breathing circuit to ambient atmosphere are provided irrespective of the primary flow of breathing gas to the patient provided by the ventilator because exhaust valve 80 functions independently of the operation of the ventilator.

Exhaust valve 80 is configured such that the rate of flow of gas to atmosphere through the valve is substantially constant over a range of pressures corresponding to the range of pressures provided in the first tube during normal operation of the ventilation system. Such pressure variations in the breathing circuit occur due to changes in the primary flow of breathing gas provided by the ventilator. As a result of the use of this exhaust valve, there is no net accumulation of volume in the breathing circuit, and, hence, no over-inflation of the patient's lungs even though the insulation gas is continuously provided to the patient. Furthermore, as noted above, the TGI system is essentially "transparent" to the ventilator, in that no special modification need be made to the ventilator or its operation in order to provide the insulation gas to the patient.

The prevent invention contemplates using exhaust valve 80 in combination with vent assembly 70 in which stagnation pressure is minimized or eliminated as discussed above, so that the dual benefits of preventing over-inflation and minimizing stagnation pressure are achieved. However, the present invention also contemplates using exhaust valve 80 alone, without vent assembly 70. While this latter embodiment may result in some amount of stagnation pressure being generated in the patient, such pressure may be acceptable in some situations or held to acceptable levels by, for example, limiting the rate at which the insufflation gas is provided to the patient. Further, this embodiment, in which only exhaust valve 80 is provided on the first tube, is beneficial in that the phasic approach to insufflation can be replaced in favor of providing a continuous flow of secondary breathing gas to the airway of the patient to flush out expired gases. As noted above, providing a continuous flow of insufflation gas is relatively simple and inexpensive and by using exhaust valve 80, the insulation system of the present invention avoids over-inflation. Also, the use of exhaust valve 80 avoids the need to "fool" the ventilator to account for the extra gas being introduced into the patient to prevent over-inflation, so that the operating capabilities of the ventilator can be maximized and the other disadvantages associated with the conventional continuous TGI technique can be avoided.

The present invention contemplates that exhaust valve 80 can have any configuration that provides a substantially constant rate of exhaust over the desired operating pressures. However, in the exemplary illustrated embodiment, exhaust valve 80 includes a housing 84 with a first opening 86 to the interior of first tube 62 and a second opening 88 to ambient atmosphere. A diaphragm 90 is provided within housing 84, and an opening 92 is provided in a portion of the diaphragm 90 on a side of housing 84 generally opposite second opening 88. Exhaust gas flows from opening 92, through a channel 94 between diaphragm 90 and housing 84, and out opening 88. Increases in pressure within first tube 62 cause diaphragm 90 to deflect upward. This upward movement decreases the cross-sectional area of channel 94 reducing the flow therethrough, thereby providing a constant exhaust flow to atmosphere even though the pressure within the first tube varies.

An example of a suitable valve that provides these functions is described in U.S. Pat. No. 5,685,296 to Zdrojkowski et al., entitled, "Flow Regulating Valve and Method," the contents of which are incorporated herein by reference into the present application. However, as noted above, the present invention contemplates that any valve that provides these functions can be used in the insufflation system of the present invention.

In the above embodiment, exhaust valve 80 is described as continuously venting gas to atmosphere at a rate that substantially matches the rate at which insufflation gas is delivered to the patient. It is to be understood, however, that exhausting the gas from the breathing circuit need not be done continuously, i.e., in a non-interrupted fashion. On the contrary, the present invention contemplates that the exhaust vent system of the present invention discharges gas from the patient circuit in discrete amounts so long as the rate at which the gas is exhausted substantially matches the rate at which the insufflation gas in delivered to the patient during a time period, such as a breathing cycle.

The present invention contemplates providing the insufflation system of the present invention as an attachment for a conventional ventilation system. According to one embodiment of the present invention, the attachment includes insufflation catheter 66, including the bi-directional vent at the distal end thereof, and a portion of the first tube to which the second tube is attached. Such an attachment would simply insert into a conventional breathing circuit by coupling the portion of the first tube into that circuit with the second tube being placed in the patient. Because this embodiment of the attachment does not include exhaust valve 80, it is optimally suited for use with a phasic TGI system. However, by including exhaust valve 80 in the attachment assembly, the insufflation system of the present invention can be used with a conventional ventilation system as a continuous TGI system without the need to significantly reconfigure the ventilation system. The dashed lines in FIG. 2 illustrate exemplary points of attachment in the breathing circuit for the portion of the first tube to which the second conduit and exhaust valve are attached. Thus, the attachment can be readily inserted into a conventional ventilation system at existing coupling locations for providing insufflation of the patient's airway.

A second embodiment of a vent assembly 94 suitable for use at the distal end portion of insufflation catheter 66 is illustrated in FIGS. 3A and 3B. Vent assembly 94 is either attached to or integrally formed with insufflation catheter 66 and includes a housing 96 that receives the flow of insufflation gas from insufflation catheter 66. A first port 98 defined in a first end portion 100 of housing 96 directs a first portion of the secondary flow of breathing gas in the first direction, as illustrated by arrow 74 in FIG. 2. A second port 102 defined in a second end portion 104 of housing 96 directs a second portion of the flow of insufflation gas in the second direction, as illustrated by arrow 78 in FIG. 2. A channel 106 in housing 96 divides the flow of insufflation gas received from insufflation catheter 66 into the first and second portions and communicates these portions to first and second ports 98 and 102, respectively. The present invention contemplates that vent assembly 94 is formed separately from the remainder of insufflation catheter 66 and fixed thereto during manufacture or forming vent assembly 94 as an integral portion of the insufflation catheter.

A potential concern with vent assemblies 70 and 94 is blockage of the exhaust ports. For example, second port 102 may become blocked, either completely or partially, if second end portion 104 slips under the distal rim of first tube 62 or if the patient's tissues or secretion collect near the exhaust ports. To minimize this concern, FIG. 4 illustrates a positioning assembly 108 for maintaining insufflation catheter 66 at a generally central location within first tube 62. Positioning assembly 108 includes a collar 110 secured to insufflation catheter 66 and spokes 112 coupled to collar 108 that keep insufflation catheter 66 spaced apart from first tube 66. Preferably, at least three spokes are provided to maintain insufflation catheter 66 at a generally central axial location within first tube 62, thereby ensuring that flows 74 and 78 of gas are not blocked. It is further preferable that spokes 112 are made from a flexible material so that the spokes deflect toward insufflation catheter 66 to maintain the insufflation catheter in the central location. It is to be understood that the positioning assembly can be configured such that the insufflation catheter, or at least the distal end of the insufflation catheter, is maintained at a location other than generally along the central axis of the first tube. This can be accomplished, for example, by making the spoke or spokes on one side of the collar shorter than the spokes on the other side.

FIGS. 5A-5D illustrate a third embodiment for a vent assembly 114 that attaches to or is integral with the distal end of insufflation catheter 66. Vent assembly 114 includes a first channel 116 that receives the distal end of insufflation catheter 66. In operation, a first portion 74 of the flow of insufflation gas is expelled from a pair of exhaust ports 118 in a direction generally toward the patient's lungs. A second portion 78 of the flow of insufflation gas is expelled from a pair of exhaust ports 120 in a direction generally opposite the first direction, i.e., away from the patient's lungs. A second channel 122 communicates the flow of insufflation gas from the insufflation catheter to exhaust ports 118, and a third channel 124 communicates the flow of insufflation gas from the insufflation catheter to exhaust ports 120 so that gas is expelled in a direction generally opposite the direction of the first flow 74. When insufflation catheter 66 is inserted into first channel 116, the exterior surface of insufflation catheter 66 defines one of the walls of third channel 124 so that second flow 78 of insufflation breathing gas is expelled from vent assembly 114 on either side of the insulation catheter. The embodiment of vent assembly 114 illustrated in FIGS. 5A-5D provides multiple exhaust ports on each side of the exhaust vent to minimize the likelihood of blockage of the ports. Thus, the embodiment of FIGS. 5A-5D avoids the need to employ the positioning assembly of FIG. 4.

FIGS. 6A-6D illustrate a fourth embodiment for a vent assembly 126 that attaches to or is integral with the distal end of insulation catheter 66. Vent assembly 126 is similar to vent assembly 114 of FIGS. 5A-5D except that the exterior surface of the vent assembly 126 is more streamlined for minimizing flow resistance to the primary flow of breathing gas. The generally rounded contours of vent assembly 126 also minimize friction with the surrounding structures or tissues so that the insulation catheter can be readily inserted into the patient at the proper position and retracted as well.

Vent assembly 126 includes a first channel 128 that receives the distal end of insulation catheter 66. In operation, a first portion 130 of the flow of insulation gas is expelled from a pair of exhaust ports 132 in a direction generally toward the patient's lungs. A second portion 134 of the flow of insulation gas is expelled from a pair of exhaust ports 136 in a direction generally opposite the first direction, i.e., away from the patient's lungs. A second channel 138 communicates the flow of insulation gas from the insufflation catheter to exhaust ports 132, and a third channel 140 communicates the flow of insufflation gas from the insulation catheter to exhaust ports 136 so that gas is expelled in a direction generally opposite the direction of the first flow 130. When insufflation catheter 66 is inserted into first channel 128, the exterior surface of insufflation catheter 66 defines one of the walls of third channel 140 so that second flow 134 of insufflation gas is expelled from vent assembly 126 on either side of the insulation catheter.

Figure 7:
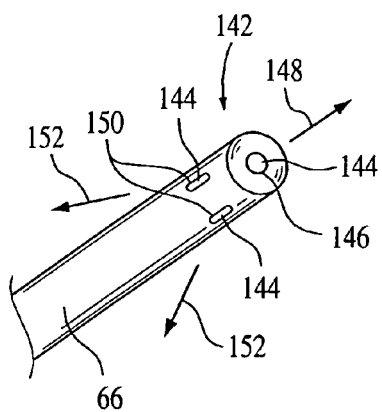
FIG. 7 is a perspective of a further embodiment of a vent assembly that directs the flow of insufflation gas from the distal end of an insufflation catheter according to the principles of the present invention.
Figure 8:
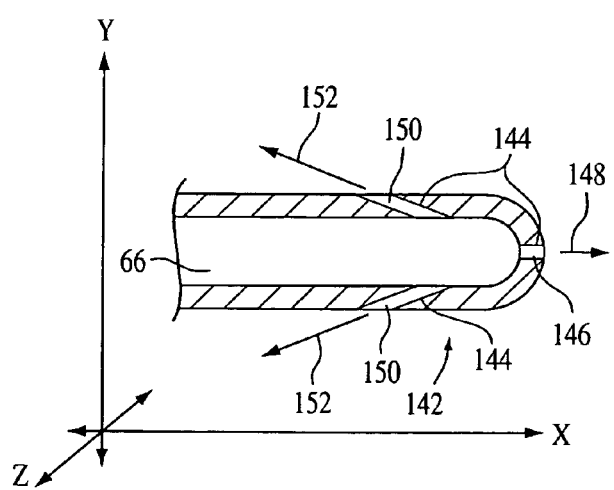
FIG. 8 is a cross-sectional view of the distal end of the insufflation catheter shown in FIG. 7.

FIGS. 7 and 8 illustrate a fifth embodiment of a vent assembly 142. In this embodiment, vent assembly 142 is defined by providing a plurality of exhaust ports 144 directly in the distal end of insulation catheter 66. As in the previous embodiments, a first set of ports 146 direct a first portion of the flow of insulation gas 148 in a first direction generally toward the patient's lungs, and a second set of ports 150 direct a second portion of the flow of insufflation gas 152 in a second direction generally away from the patient's lungs. The present invention contemplates that each set of ports can include one or more exhaust ports.

The first and second sets of exhaust ports are defined in insufflation catheter 66 such that the vector forces associated with first and second portions 148 and 152 of the flow of insulation gas therefrom are offsetting along the proximal/distal axis, i.e., the lengthwise axis of the catheter. For example, as shown in FIG. 8, first and second sets of ports 146 and 150 are configured and arranged relative to one another such that the net of the vector forces associated with the flow of gas along the x-axis is substantially zero. In addition, the exhaust ports in the second set of ports are configured and arranged such that the net of the vector forces associated with the flow of gas along the y-axis is also substantially zero. It should be noted that in this embodiment, there is no y-component associated with the vector force produced by first portion 148 of breathing gas exiting from exhaust port 146. As a result of this configuration, the net or the vector forces associated with the discharge of insufflation gas from the insulation catheter in the first direction generally toward the lungs and in the second direction generally away from the lungs is substantially zero, so that substantially no stagnation pressure is generated as a result of injecting the insufflation gas into the patient's airway. Although not shown in FIGS. 7 and 8, it should be further noted that the exhaust ports in the second set of ports are preferably configured and arranged around the circumference of insufflation catheter 66 such that the net of the vector force components associated with the flow of gas in the yz-plane is also substantially zero.

As noted above, the present invention also contemplates forming the first and second sets of ports such that the net of all the second vector force components in the second direction, i.e., in the negative x direction in FIG. 8, is greater than the net of all the first vector force components in the first direction, i.e., in the positive x direction. As a result, the pressure drop created by the presence of the insufflation catheter in the patient circuit is offset, and there is no significant positive stagnation pressure created in the patient as a result of the flow of insufflation gas exiting the insufflation catheter via the first and second ports.

Figure 9A:
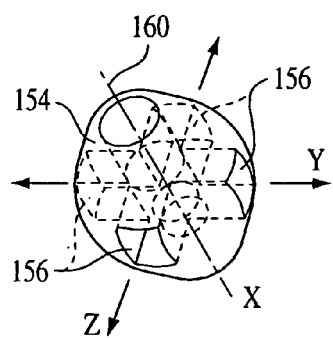
FIGS. 9A-9C are perspective, top, and side views illustrating a still further embodiment of a vent for directing the flow of insufflation gas from the distal end of the insufflation catheter according to the principles of the present invention.
Figure 9B:
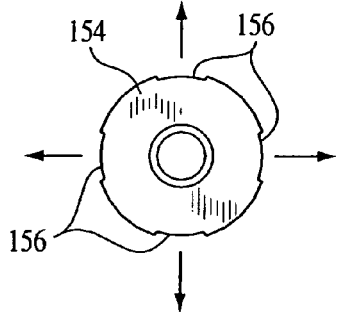
Figure 9C:
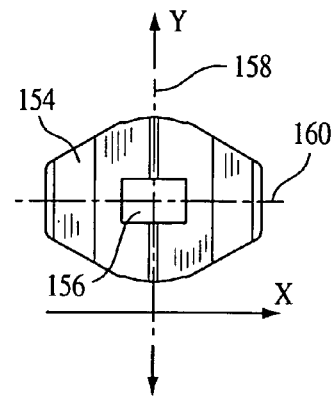

FIGS. 9A-9C illustrate a sixth embodiment of a vent assembly 154 that attaches to or is integral with the distal end of insufflation catheter 66. In this embodiment, vent assembly 154 includes a plurality of exhaust ports 156 that lie in generally the same plane, which corresponds to the yz-plane located along a lateral axis 158 of the vent assembly. Balancing of the forces in the axial direction of insufflation catheter 66, i.e., along the x-axis shown in FIGS. 9A and 9C, is accomplished in this embodiment because there are no vector components for the flow of insufflation gas in the x-direction (positive or negative). That is, by directing the insufflation gas in a substantially lateral direction within a patient, which is generally perpendicular to the first and the second directions (along the x-axis), so that the flow of insufflation gas is directed neither into nor out of the patient's respiratory system, the net of all vector force components in a first and second directions resulting from the discharge of the flow of insufflation gas into the patient's airway by the vent assembly is substantially zero. Thus, no stagnation pressure is generated. It is believed, however, that because there are no vector components for the flow of insufflation gas in the positive x-direction, i.e., directed into the patient's respiratory system, this embodiment of the present invention may not provide optimize the gas purging function as well as the other embodiments because it does not direct a stream of gas generally into the lungs.

In the embodiment illustrated in FIGS. 9A-DC, the net of the vector forces associated with the flow of insufflation gas from ports 156 in the yz-plane, which is a plane in which lateral axis 158 lies, is also zero. This is accomplished by providing a symmetrical distribution of the flows from vent assembly 154 about a central axis 160. Thus, by directing the flow of insufflation gas in a lateral direction, this embodiment of the vent assembly for use in the TGI system of the present invention ensures that the net vector forces associated with the discharge of insufflation gas from the insufflation catheter in the first and second directions (into and out of the patient) are substantially zero, so that substantially no positive or negative stagnation pressure is generated as a result of injecting the flow of insufflation gas into the patient's airway. In addition, the discharge of insufflation gas in the yz-plane is arranged such that the net of the vector forces in the y-plane is also zero. Thus, the total net forces in all directions is also zero for this embodiment.

In this embodiment, the vector forces in the yz-plane are offsetting (balanced) due to the symmetrical distribution of flow from the vent assembly about axis 160. It is to be understood, however, that the net vector forces in the yz-plane, i.e., in a lateral direction, which is generally perpendicular to the longitudinal axis of the insufflation catheter, need not be offsetting. If this is the case, the distal end of the catheter will be urged in a certain direction opposite the side of the catheter releasing the greater net vector flow. If the distal end of the insufflation catheter is within the endotracheal or tracheal tube, it will be urged against the inside wall of the tube. Likewise, if the distal end of the insufflation catheter is outside the endotracheal or tracheal tube, it will be urged against the patient's tissues. Either of these outcomes may be acceptable so long as the insufflation catheter accomplishes its function of discharging insufflation gas into the patient's airway while minimizing the generation of stagnation pressures. It is to be further understood that the number of ports defined in the vent assembly can be varied. However, it is preferable that the number and location or pattern of the ports be provided such that the net vector forces in the y-direction are balanced.

In the embodiment illustrated in FIGS. 9A-9C, vent assembly 154 is an element that is provided on the distal end of the insufflation catheter. It is to be understood, however, that the vent assembly illustrated in FIGS. 9A-9C, where the flow of insufflation gas is provided in only the lateral direction, can be accomplished by defining exhaust ports 156 directly in the distal end of insufflation catheter 66, as done in the embodiment illustrated in FIGS. 7 and 8. Such an arrangement has many advantages, including, for example, decreasing the size of the distal end of the insufflation catheter, minimizing the number of parts for the TGI catheter, and reducing manufacturing costs. In addition, the lateral discharge of insufflation gas within the patient can be accomplished by locating the distal end of the insufflation catheter within the patient such that the stream of insufflation gas is directed neither into nor out of the patient's respiratory system.

Figure 10:
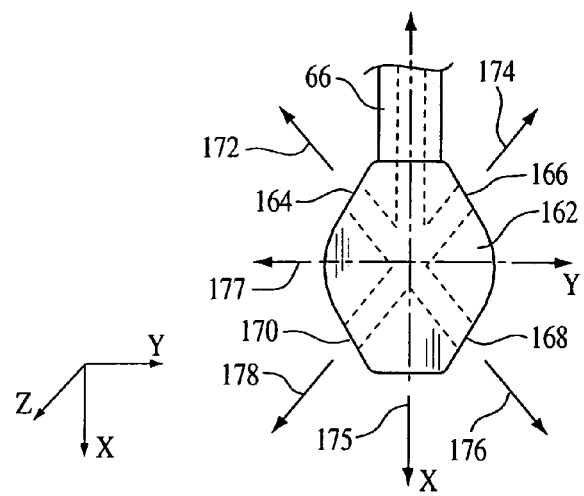
FIG. 10 illustrates another embodiment of a vent for directing the flow of insufflation gas from the distal end of the insufflation catheter.

It can be appreciated from the six embodiments described above, that there are a variety of ways in which the secondary gas can be directed from the distal end of the insufflation catheter while minimizing, and preferably eliminating, the creation of stagnation pressure. FIG. 10 illustrates yet a seventh example of a vent assembly 162 for accomplishing this purpose. Vent assembly 162 attaches to or is integral with the distal end of insufflation catheter 66.

In FIG. 10, vent assembly 162 includes a plurality of ports 164-170 that direct the flow of insufflation gas from the vent assembly as indicated by arrows 172-178, which are at a non-zero angle relative to longitudinal axis 175 of the insufflation catheter. Ports 164-170 are disposed on vent assembly 162 such that the vector forces resulting from the injection of insufflation gas from the vent assembly that are parallel to the x-axis (longitudinal axis 175) are offsetting, i.e., so that there is substantially no net vector force along the x-axis. As noted above, this configuration reduces or eliminates the creation of a stagnation pressure in the patient. It is preferable that the vector force components resulting from the injection of insufflation gas from the vent assembly that are parallel to the y-axis (lateral axis 177) are also offsetting, i.e., so that there is substantially no net vector force along the y-axis or the z-axis. It is to be understood, however, that a balancing of forces in the yz-plane is not necessary for the purpose of eliminating stagnation pressure. Although four ports are illustrated in FIG. 10, it is to be understood that as few as two or more than four ports can be provided so long as the balancing function, where the net vector force into and away from the patient's lungs are substantially zero, is achieved.

In all of the seven above-described embodiments, the ports direct the flow of insufflation gas from the vent assembly such that the vector forces of the flow of insufflation gas, at least with respect to the x-axis, are offsetting. That is the net flow down in FIG. 10 (generally toward the patient's lungs) is offset by an equal net flow up (generally away from the patient's lungs). The result of this balancing of the net vector forces in the x-direction is a minimization or elimination of stagnation pressures in the patient that would otherwise result from the injection of the flow of insufflation gas into the patient's respiratory system. Please note that the x and y coordinates in FIG. 10 are intentionally oriented in the manner illustrated, i.e., rotated from what is generally considered conventional, to correspond with the orientation for these coordinates shown in FIGS. 8 and 9C, where the x-axis is parallel to the longitudinal axis of the insufflation catheter.

One can appreciate that reducing or preventing the generation of a stagnation pressure does not require that the flows from the vent assembly be directly opposite one another, such as up and down shown in FIGS. 2-6C. Quite the contrary, as shown in FIGS. 7, 8, and 10, the flows from the vent assembly can be provided in a variety of directions so long as the net vector force components generally toward the patient's lungs (into the patient) are offset by a substantially equal net vector force component generally away from the patient's lungs (out of the patient).

Figure 11:
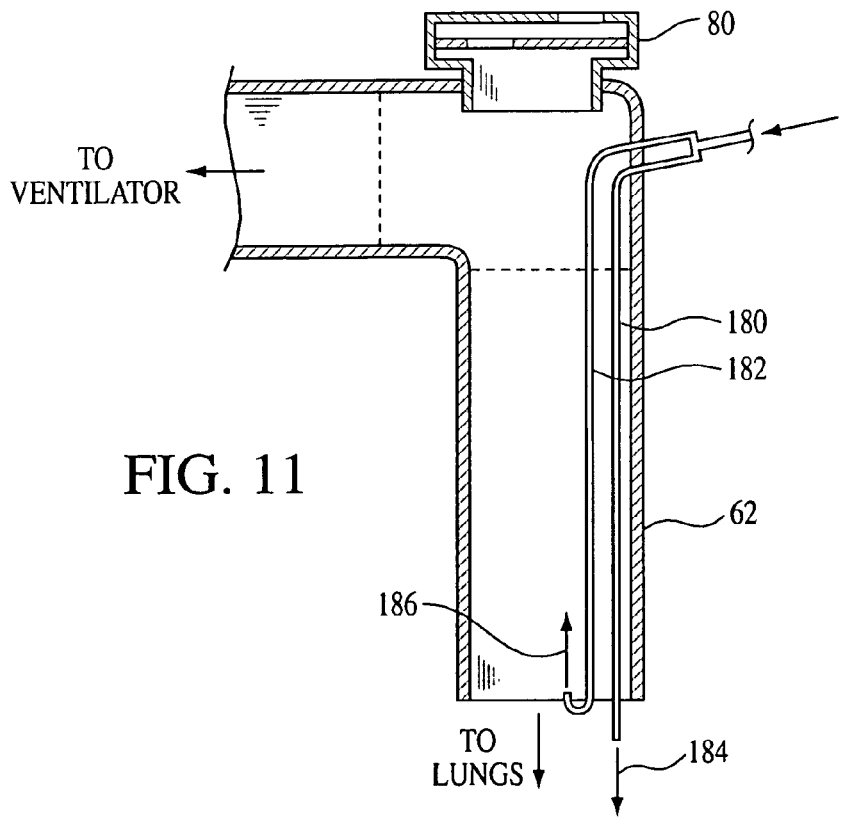
FIG. 11 is a sectional view of a portion of a breathing circuit illustrating the insufflation system according to yet another embodiment of the present invention.
Figure 6A:
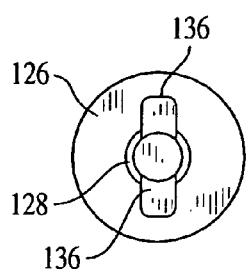
FIGS. 6A-6C are top, side and bottom views, respectively, illustrating yet another embodiment of a bi-directional vent for directing the flow of insulation gas in opposite directions from the distal end of the insulation catheter.
Figure 6B:
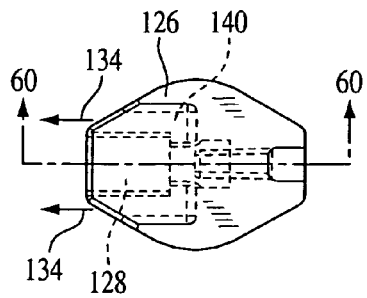
Figure 6C:
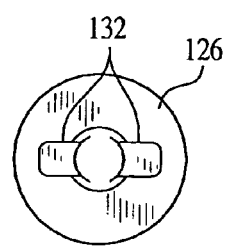
Figure 6D:
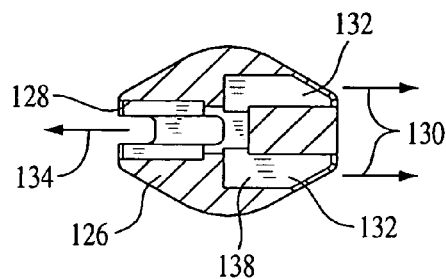
FIG. 6D is a sectional view taken along line 6D-6D in FIG. 6B.

A still further embodiment of the present invention is illustrated in FIG. 11. In the previous embodiments, the TGI system includes a single insufflation catheter with a vent assembly at its distal end, where the vent assembly includes one or more ports for directing the flow of insufflation gas in an offsetting or zero net force fashion. In the embodiment shown in FIG. 11, however, a pair of insufflation catheters 180 and 182 are provided in first tube 62 in place of the single insufflation catheter 66 of the previous embodiments. More specifically, first insufflation catheter 180 is a generally straight tube that directs a portion of the flow of insulation gas in a first direction indicated by arrow 184 generally toward the patient's lungs or into the patient. Second insulation catheter 182, on the other hand, has a distal end portion that directs another portion of the flow of insufflation gas in a second direction indicated by arrow 186, which is generally opposite the first direction, i.e., generally away from the patient's lungs or out of the patient. The flow in insufflation gas in direction 186 produces a negative stagnation pressure that offsets or cancels out the positive stagnation pressure created by the flow of insufflation gas out of first insufflation catheter 180. As noted above, it is not necessary that flows 184 and 186 be directed exactly as shown so long as the vector forces in the first and second directions into and out of the patient along the patient's airway associated with the two flows are offsetting, so that substantially no stagnation pressure is generated in the patient. Of course, the insufflation catheters can be configured to provide more than one flow and more than two catheters can be provided, so long as the net vector force of all of the flows of the secondary gas from all of the insufflation catheters in the lengthwise axial direction is substantially zero.

In a preferred embodiment of the present invention, the proximal ends of insulation catheters 180 and 182 are commonly connected to the source of secondary breathing gas so that the flows 184 and 186 out of insulation catheters 180 and 182, respectively, are substantially equal and, hence, offsetting. It is to be understood, however, that each insulation catheter can be supplied with gas from an independent gas source.

As with the embodiment illustrated in FIG. 2, the insulation system of FIG. 11 can be configured as an attachment for a conventional ventilation system. For a phasic TGI system, exhaust valve 80 need not be provided in the attachment. The dashed lines in FIG. 11, like those in FIG. 2, illustrate exemplary coupling locations for the portion of first tube 62 in the breathing circuit, with insufflation catheters 180 and 182 being directed into the endotracheal or tracheostomy tube for removing exhaled gases, once the portion of the first tube between the dashed lines is coupled in the breathing circuit.

Figure 12:
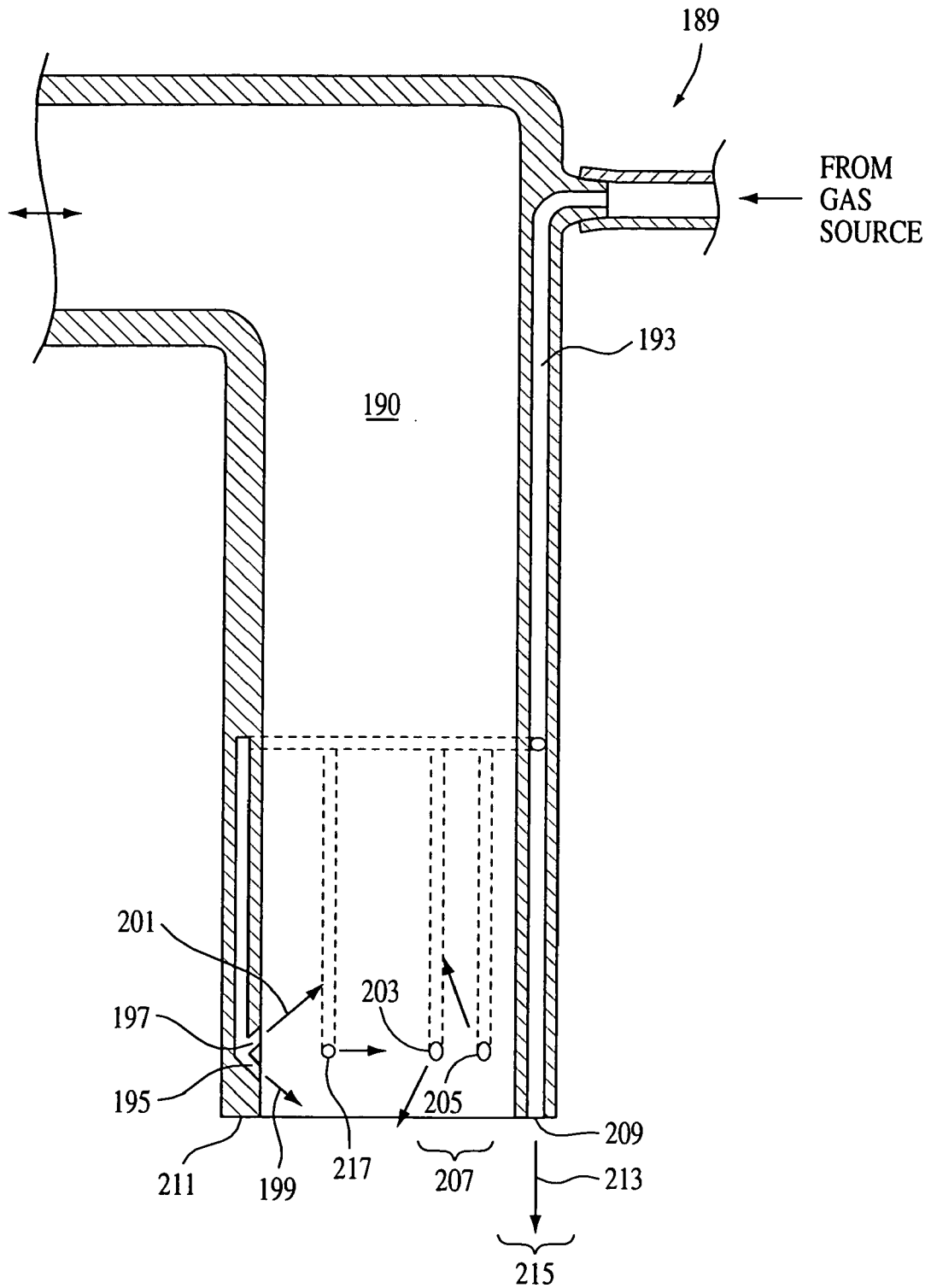
FIG. 12 is a sectional view of a distal end portion of a breathing circuit illustrating a further embodiment of an insufflation system of the present invention.

The embodiment illustrated in FIG. 11 is advantageous in that it simplifies the structure for simultaneously providing a flow of insufflation gas in opposing directions within the patient's airway. However, this embodiment requires providing multiple insufflation catheters within first tube 62, which may increase the resistance to flow through the first tube. This can be minimized, however, by providing at least a portion of insufflation catheter 180 and/or insufflation catheter 182 integral with or within the wall of first tube 62. The present invention also contemplates providing the entire length of one or both on the insufflation catheters within the wall of first tube 62. FIG. 12 illustrates an embodiment of the present invention in which the insufflation catheter is formed as a conduit provided in the wall of first tube, which is typically an endotracheal or nasotracheal tube. For the sake of illustration, FIG. 12 illustrates a variety of techniques by which the insufflation gas can be delivered to the patient using an insufflation catheter formed within the wall of the distal portion of the breathing circuit, e.g., the endotracheal or nasotracheal tube. The present invention contemplates using any one of these techniques or any combination of these techniques to deliver the insufflation gas to the airway of the patient. This embodiment of the present invention is advantageous in that it eliminates the resistance to flow within the endotracheal or nasotracheal tube imposed by the insufflation catheter. This flow restriction causes by the present of the insufflation catheter in the breathing circuit is also believed to be a factor that contributes to the increased autoPEEP in conventional TGI system because the patient must exhaled against a more restricted flow than would otherwise be the case without the presence of the TGI system.

As shown in FIG. 12, insufflation system 189 includes a first tube 191 that inserts into a patient's airway for providing a primary flow of breathing gas to the patient. A conduit 193 is defined within the wall of first tube and a port 195 is provided for coupling conduit 193 to an insufflation gas source (not shown). Conduit 193 carries the insufflation gas to the distal end portion of first tube 191 in the same manner as insufflation catheter 66. In the previous embodiments, the vent assembly is configured so as to discharge gas from the insufflation catheter generally in a first direction toward the patient and in a second direction generally out of a patient so that the net vector components in the lengthwise direction are substantially zero, thereby minimizing the generation of stagnation pressure in the patient. This same function is achieved in this embodiment by controlling the direction of flow for the insufflation gas exiting conduit 193. FIG. 12 illustrates several techniques for discharging insufflation gas from the distal end of first tube 190.

According to a first technique, a pair of ports 195 and 197 are provided to communicate the insufflation gas from a conduit 193 to the airway of the patient. Port 195 directs a first portion of the flow of insufflation gas in the first direction, as indicated by arrow 199, generally toward the patient's lungs, and port 197 directs a second portion of the flow of insufflation gas in the second direction, as indicated by arrow 201, generally away from the patient's lungs. As in the previous embodiments, the vector components associated with first and second flows 199 and 201 of insufflation gas are preferably offsetting, at least along the lengthwise axis of catheter 190, so that no stagnation pressure is generated in the patient. According to a second technique, this same result is achieved by providing two or more separate ports 203 and 205 in the wall of tube 190, with each port directing a portion of the flow of insufflation gas either generally toward or generally away from the lungs of the patient.

Instead of providing a pair of ports 207 in the inside wall of first tube 190, a third technique of delivering the insufflation gas from tube 190 includes providing a port 209 in a distal surface 211 of the first tube to direct a portion 213 of the flow of insufflation gas in the first direction generally toward the patient's lungs. This embodiment is believed to be advantageous in that is directs a portion of the insufflation gas directly into or down the patient's airway. A second port, such as port 205, is provided to deliver another portion of the insufflation gas in a second direction generally out of the patient so that flow 213 is offset by the flow out of port 205 so that a pair of ports 215 accomplish the same function of no net stagnation pressure as the vent assembly of the previous embodiments.

The present invention contemplates that other ports, such as port 217, can be provided on the inside wall of tube 190 to direct a portion of the insufflation gas laterally, as discussed above with respect to FIGS. 9A-9C. In addition, the present invention contemplates providing one or more ports for directing the insufflation gas as described above one the outside wall of tube 190. However, it is believed that such a configuration would not be advantageous due to the small clearance that is believed to exist between the outside wall of tube 190 and in surface of the patient's airway.

FIG. 12 illustrates a variety of techniques for discharging the insufflation gas from a conduit defined in the wall first tube 190. The present invention contemplates using any one of these techniques, or any combination of these techniques, to deliver the insufflation gas to the airway of the patient. For example, multiple ports similar to port 209 can be provided in the distal end of tube and multiple ports similar to port 205 can be provided to deliver the offsetting flow of insufflation gas.

As discussed above, the present invention contemplates using the insufflation with a continuous flow TGI system by providing exhaust valve 80 in a portion of first tube 62. Exhaust valve 80 continuously exhausts gas from the first tube at substantially the same rate as the flow of insufflation gas is introduced into the breathing circuit to produce a balance between the amount of gas introduced to the breathing circuit and the amount of gas exhausted from the breathing circuit. As a result, there is no net increase or decrease in the amount of gas in the breathing circuit. This requires regulating the flow rate of the insufflation gas into the TGI system and/or regulating the flow of exhaust gas from the system so that the two flow rates are substantially equal.

In the above described embodiment, exhaust valve 80 exhausts gas from the system at a rate that cannot be changed unless the exhaust valve is replaced with another exhaust valve having a different exhaust flow rate. That is, exhaust valve 80, due to its fixed configuration, exhausts gas at a given rate. For this reason, in operation, the caregiver or user of the TGI system must regulate the rate of flow of the insufflation gas into the patient to match the given rate of exhaust from exhaust valve 80. It is preferable, however, to allow the caregiver greater flexibility in selecting the rate at which the flow of insulation gas is introduced to the patient without having to take into consideration the exhaust rate of the exhaust valve. Techniques for accomplishing this function are discussed below with reference to FIGS. 13-15.

Figure 13:
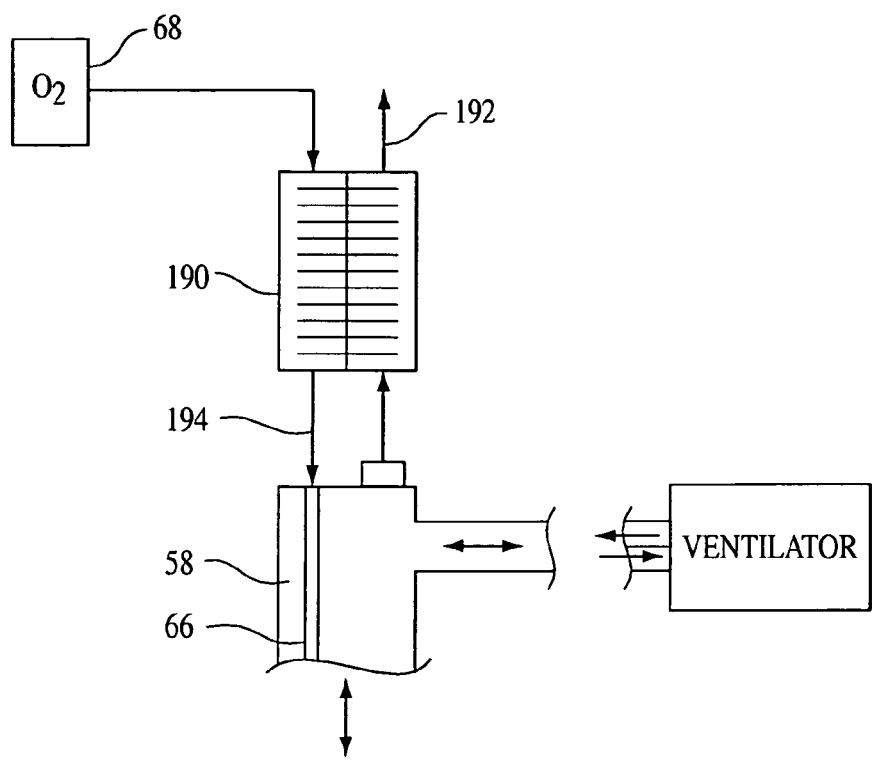
FIGS. 13 and 14 schematically illustrate other embodiments for an insufflation system according to the principles of the present invention.

In the embodiment shown in FIG. 13, a flow control assembly 190 is provided that ensures that the rate at which gas is exhausted from the breathing circuit, as indicated by arrow 192, substantially matches the rate at which the insufflation gas is introduced into the patient's airway, as indicated by arrow 194. An example of a suitable flow control assembly for accomplishing this function is a paddlewheel valve, wherein the incoming gas flow 194 turns one side of a paddlewheel 196. The other side of paddlewheel 196 is provided in the exhaust path from the breathing circuit 58. The paddlewheel in configured such that turning one side of the wheel via flow 194 draws out or allows an equal amount of flow 192 to exit the breathing circuit. As a result, there is no net accumulation of gas in the breathing circuit. Because the rate of flow 194 into the breathing circuit via the TGI system controls the speed at which the paddlewheel turns, and, hence, the rate at which flow 192 exhausts from the breathing circuit, the caregiver can freely select any rate of flow for the introduction of the insulation gas into the patient and flow control assembly 190 will automatically ensure that a substantially equal exhaust flow is provided from the breathing circuit.

While FIG. 12 illustrates a paddlewheel configuration for flow control assembly 190 to ensure that the flow out of the breathing circuit is substantially the same as the flow into the breathing circuit provided by the insulation catheter, it is to be understood that the present invention contemplates other configurations for flow control assembly 190 that accomplish this function. For example, a flow or volume meter can be provided that measures the rate or volume of gas introduced into the breathing circuit via the TGI system, and a flow control valve can be provided in the exhaust path, with the flow control valve controlling the rate of exhaust to atmosphere based on the output from the flow or volume meter.

Figure 14:
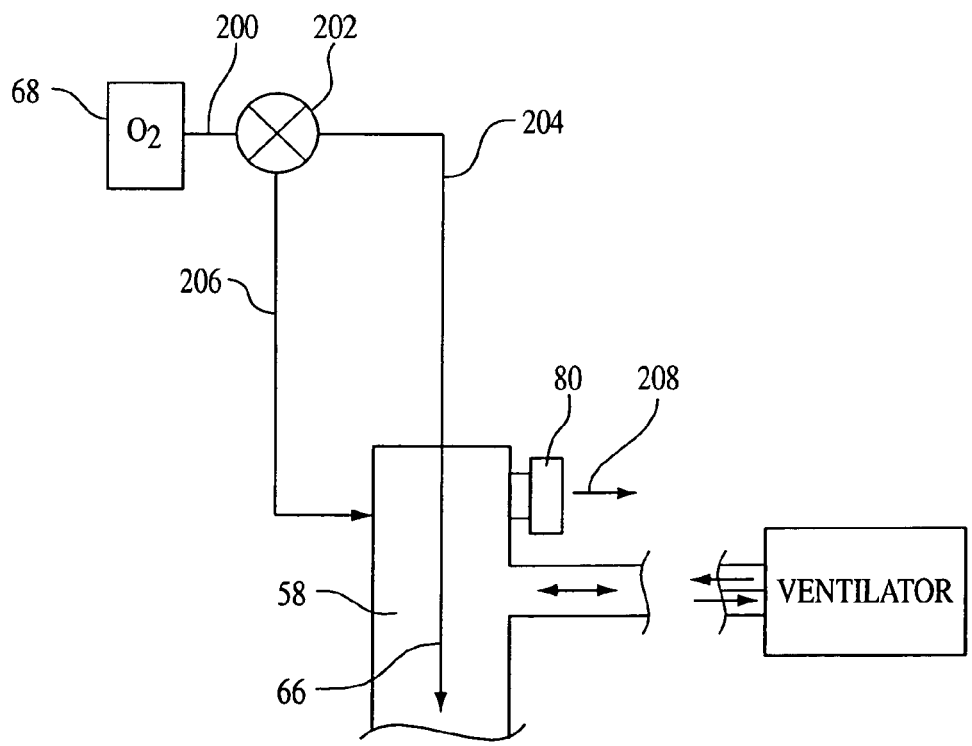

Another technique for ensuring that the flow out of the breathing circuit matches the flow of insufflation gas into the circuit provided by the TGI system while allowing the caregiver to select the rate for the flow of insufflation gas provided by the TGI system is shown in FIG. 14. In this embodiment, a first flow of gas 200 from source 68 is separated by a bypass valve 202 into a secondary flow 204 that is provided to the TGI system and a bypass flow 206. Bypass flow 206 is introduced into breathing circuit 58 at any location that allows this bypass flow to exhaust from the breathing circuit via exhaust valve 80, as discussed above.

The rate of first flow 200 and the rate of exhaust 208 from exhaust valve 80 should match one another as in the embodiment of FIG. 2. However, this embodiment allows the caregiver to select the rate at which the insufflation gas is provided by insufflation catheter 66 by selecting the flow rate for secondary flow 204, with the remainder of the first flow of gas 200 being diverted by bypass valve 202 and introduced in the breathing circuit without being delivered to the insufflation catheter. Total flow 200 into the breathing circuit, i.e., secondary flow 204+bypass flow 206, should match the total flow 208 continuously exhausted from the breathing circuit. The amount of gas provided to the breathing circuit via bypass flow 206 will change as the user or caregiver changes the amount of gas provided via the TGI system. However, the total flow into the breathing circuit will always match the total flow out of the breathing circuit regardless of the flow rate of the flow of insufflation gas provided via the TGI system. Thus, one exhaust valve 80 having an exhaust flow rate that matches the rate of first flow 200 can be used in the TGI system, while allowing the caregiver to vary the rate at with the insufflation gas (second flow 204) is delivered to the patient's airway by changing the amount of gas diverted in bypass valve 202.

It should be noted that the TGI system shown in FIG. 13, and, in particular, bypass valve 202 and/or the system for providing bypass flow 206 should be designed to account for the fact that the TGI system imposes a relatively significant flow restriction on the flow of gas to the patient's airway via insufflation catheter 66. For example, the present invention contemplates providing a flow restriction with respect to bypass flow 206, where the flow restriction imposed on bypass flow 206 substantially matches the flow restriction presented by the TGI system so that the proper amount of insufflation gas is provided to the insufflation catheter.

Figure 15:
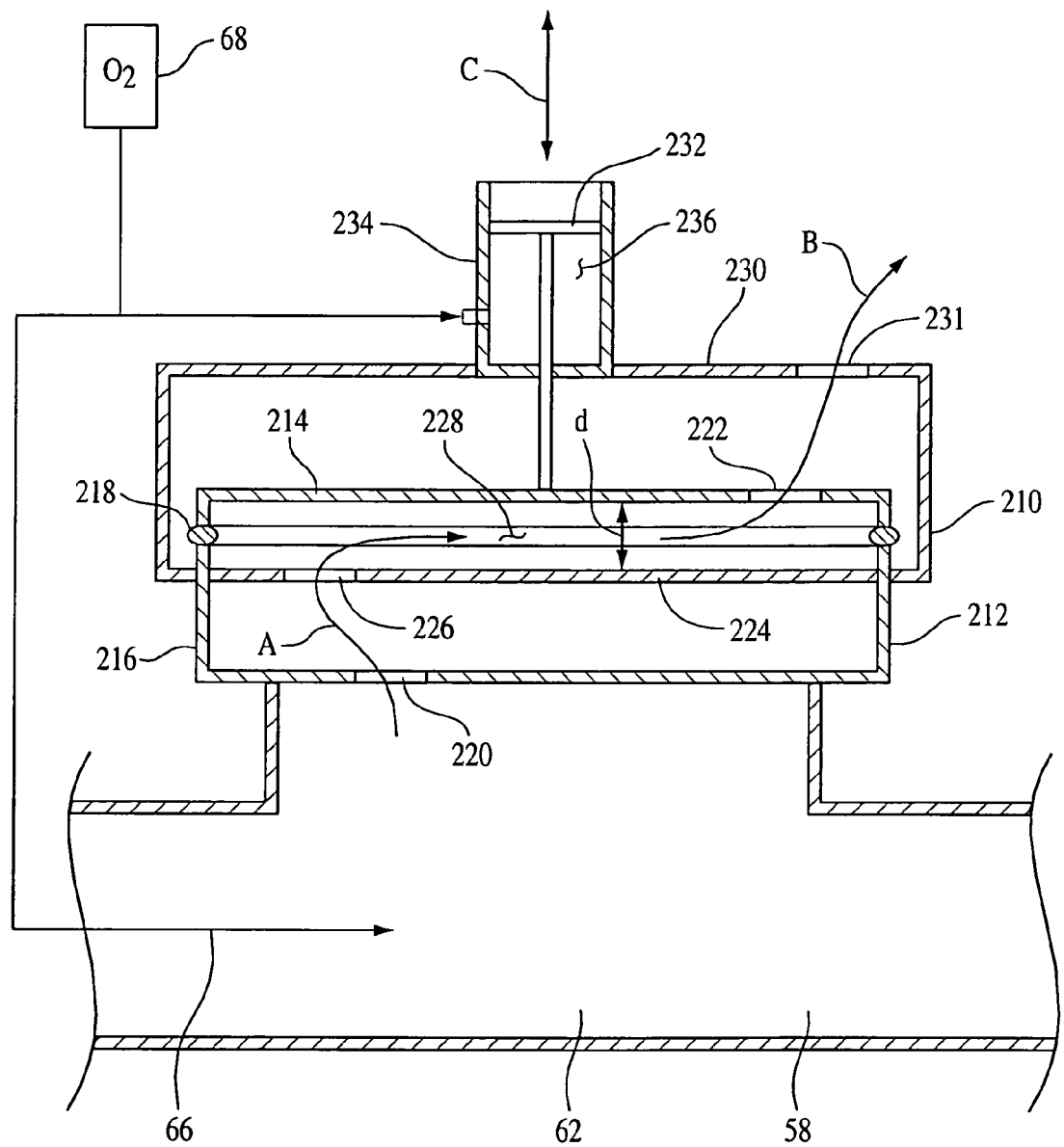
FIG. 15 schematically illustrates another embodiment for an exhaust valve for use in a tracheal gas insufflation system of the present invention.

FIG. 15 illustrates yet another technique for ensuring that the flow out of the breathing circuit matches the flow of insufflation gas into the circuit provided by the TGI system so that the caregiver has flexibility in selecting the rate for the flow of insufflation gas into the patient's airway. In this embodiment, exhaust valve 210 is configured such that the flow rate through the exhaust valve varies with the flow rate of insufflation gas delivered to the patient via the TGI system. Exhaust valve 210 is substantially similar to exhaust valve 80 in that it is a constant flow valve that allows a constant rate of exhaust from the breathing circuit to atmosphere despite fluctuations in the pressure of gas in breathing circuit 58. The main difference between exhaust valve 210 and exhaust valve 80 is that the dimensions of the exhaust pathway through the valve, such as width d of channel 228, vary in valve 210 based on the flow of the secondary gas into the patient, thereby controlling the rate at which gas vents to atmosphere through valve 210. In this respect, it can be appreciated that exhaust valve 210 provides the same general function provided by flow control assembly 190 in FIG. 13. In exhaust valve 80, the dimensions of channel 94 do not vary based on the flow of insufflation gas to the patient.

As shown in FIG. 15, exhaust valve 210 includes a housing 212 defined by a first member 214 and a second member 216, which are moveably coupled to one another via a flexible membrane 218 so that the first and second members 214 and 216 can move toward and away from one another. A first opening 220 is provided in second member 216 that communicates the interior of housing 212 with first tube 62 in breathing circuit 58, and a second opening 222 is provided in first member 214. A diaphragm 224 is provided within housing 212, and an opening 226 is provided in a portion of diaphragm 218 on a side of housing 212 generally opposite second opening 216. Exhaust gas flows from openings 220 and 226, through a channel 228 between diaphragm 224 and first member 214, and out opening 222, as indicated by arrows A and B. Exhaust valve 210 also includes a support structure 230 fixed to second member 216 for supporting a piston and cylinder arrangement that is used to move first member 214 relative to second member 216. An opening 231 is defined in support structure 230 to communicate channel 228 to atmosphere, as indicated by arrow B. A piston 232 is provided in cylinder 234 so as to define a chamber 236 that is closed relative to the ambient atmosphere. One end of piston 232 is coupled to first member 214 so that movement of the piston also moves first member 214 relative to second member 216, thereby altering the dimensions of channel 228, such as width d of channel 228, to alter the flow rate of gas from tube 62 to atmosphere.

As in the previous embodiments, a source 68 of the secondary gas is provided to the breathing circuit via insufflation catheter 66 in the TGI system. In this embodiment, however, the secondary gas also communicates with chamber 236 so that a pressure differential exists between chamber 236 on the interior side of piston 232 and ambient atmosphere on the exterior side of piston 232. Communicating the flow of insufflation gas to chamber 236 causes piston 232 to move, as indicated by arrow C, based on the flow rate, and, likewise, the pressure level, of the flow of insulation gas into the breathing circuit. Movement of piston 232, in turn, moves first member 214 relative to second member 216, which changes the width d of channel 228, thereby changing the rate at which gas exhausts from the breathing circuit in proportion to the rate at which the flow of insufflation gas is provided to the breathing circuit via the TGI system. For example, as the rate of the flow of insulation gas increases, the pressure in chamber 236 increases, moving piston 232 upward to increase the dimensions of channel 228 so that more gas exhausts from tube 62. Preferably, exhaust valve 210 is configured such that the increase or decrease in the rate of exhaust gas is substantially the same as the corresponding increase or decrease in the rate of flow of insulation gas provided by the TGI system.

Figure 16:
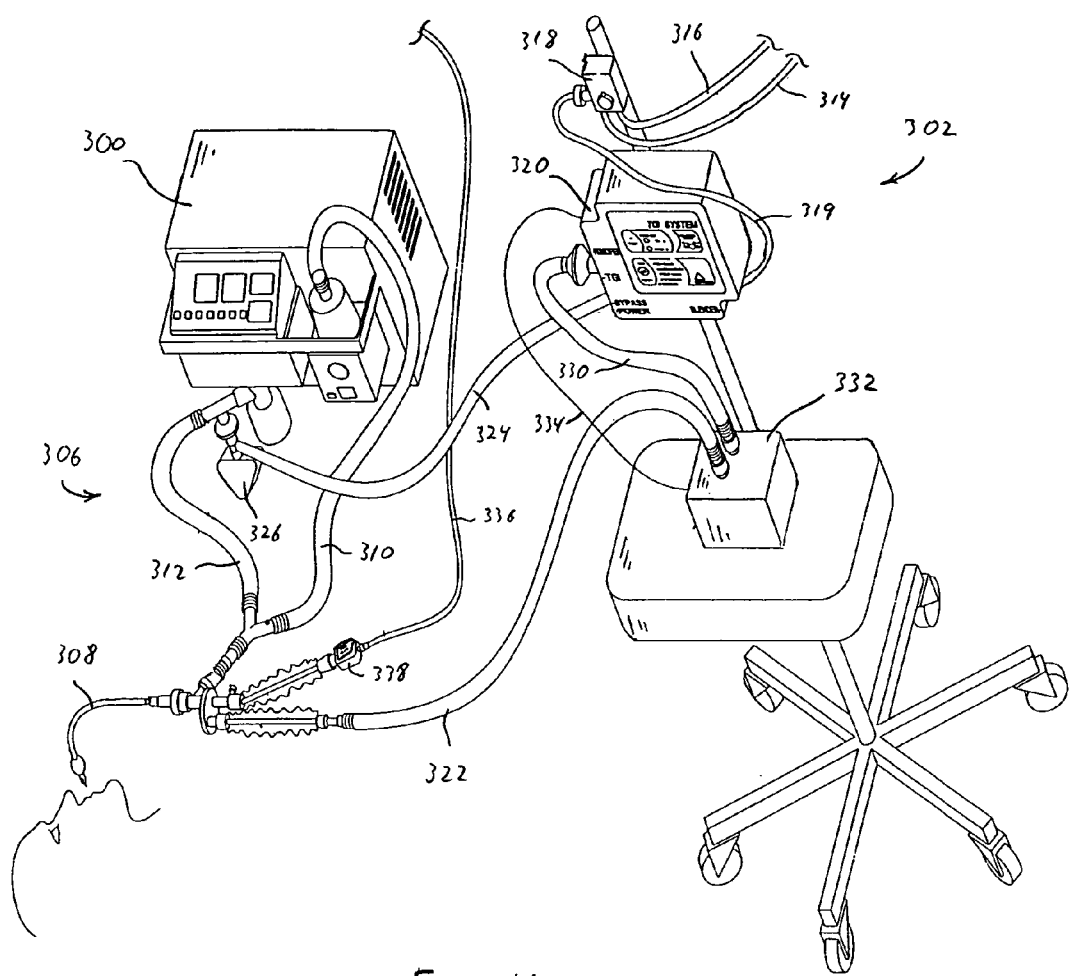
FIG. 16 is a perspective view of a ventilator and a tracheal gas insufflation system of the present invention suitable for connection to a patient.

FIG. 16 illustrates a ventilator 300 and a tracheal gas insulation system, generally indicated at 302, according to the principles of the present invention about to be connected to a patient 304. A patient circuit 306 communicates ventilator 300 with an airway of a patient. In the illustrated embodiment, an endotracheal tube 308 is shown connecting the ventilator to the patient. It is to be understood that the present invention contemplates connecting the patient and the ventilator in any conventional manner, such as via a tracheotomy tube. Patient circuit 306 includes an inspiratory limb 310 and a expiratory limb 312.

Figure 17:
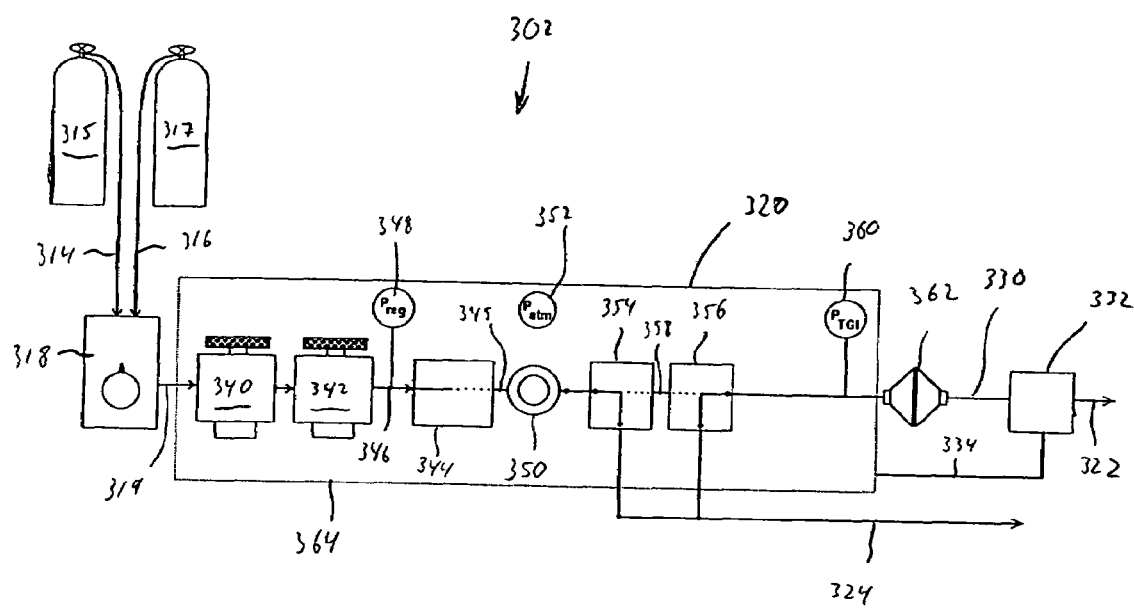
FIG. 17 is a schematic diagram of a first embodiment of a TGI flow control system according to the principles of the present invention.

TGI system 302 includes a source of TGI gas. In the illustrated embodiment, an oxygen tube 314 is connected to an source of oxygen (315 in FIG. 17) and an air inlet tube 316 is connected to a source of air (317 in FIG. 17). Oxygen tube 314 and air inlet tube 316 are connected to a blender 318 that is used to set the fraction of inspirited oxygen ($FIO_2$) to be provided by the TGI system. An outlet 319 of blender 318 is provided to a TGI flow control system 320 that is coupled between patient circuit 306, insufflation catheter 322, and the source of insufflation gas. Flow control system 320 controls a flow of gas between the patient circuit, the insulation catheter, and the source of insufflation gas.

TGI system 302 includes a first outlet line 324 that connects the TGI flow control system 320 to patient circuit 306. More specifically, outlet line 324 connects TGI flow control system 320 to expiratory limb 312. An exhaust valve 326 is provided in expiratory limb 312. In one embodiment of the present invention, exhaust valve 326 corresponds to exhaust valve 80, as discussed above, and provides a constant rate of exhaust regardless of the pressure in the expiratory limb. This enables the overall ventilation/TGI system to remove substantially the same volume of gas that is introduced into that system via the insufflation catheter in the TGI system over a given period of time, such as one respiratory cycle.

A second outlet line 330 from TGI flow control system 320 is provided to a heated humidifier 332, which heats and humidifies the gas flowing from TGI flow control system 320 into insufflation catheter 322. A control line 334 is provided from TGI flow control system 320 to heated humidifier 332 to control the operation of the heater in the heated humidifier. A processor (not shown) in TGI flow control system 320 controls the operation of heated humidifier 332 via a signal or power provided on control line 334. It is to be understood that humidifier 332 can have any conventional configuration, can be a non-heated humidifier, and can be eliminated if heat or humidification is not desired.

In the illustrated embodiment, a distal end portion of insufflation catheter 322 selectively inserts into endotracheal tube 308 to deliver the insufflation into the patient's airway. The present invention also contemplates providing a suction catheter 336 connected to a vacuum source (not shown) that is controlled by a suction control valve 338. Insufflation catheter 322 and suction catheter 336 can be alternatively placed in the patient's airway using any conventional technique. Various embodiments for TGI flow control system 320 are discussed below with respect to FIGS. 17-21.

TGI flow control system 320 controls the rate the insufflation gas is delivered to TGI system 302 and regulates the pressure of the insufflation gas. This is accomplished by means of pressure regulators 340 and 342 coupled to output line 319 from blender 318, which is the source of insufflation gas to the TGI system. It is to be understood that the two regulators shown in FIG. 17 can be replaced with a single regulator. In addition, further regulators can be added to step down the pressure as needed. In a preferred embodiment, the final pressure for the insufflation gas at the output of the last regulator is approximately 25 psi. Of course, the regulators can be eliminated if the pressure of the gas entering the TGI flow control system is already at the desired pressure.

Control system 320 also includes valving to control the flow of insufflation gas between (1) the source of insufflation gas, which correspond to output 319 of blender 318, (2) patient circuit 312 via outlet line 324, and (3) insufflation catheter 322. To this end, control system 320 includes a main shutoff valve 344 that is coupled to outlet 346 of regulator 342. An optional pressure sensor 348 is provided at an inlet to the main shut valve.

A needle valve 350 disposed in line 345 controls the rate at which the insufflation gas flows into the TGI system. It is to be understood that the present invention contemplates using any conventional technique for controlling the flow of gas to the TGI system. For example, an orifice plate can be used in place of the needle valve. Another optional pressure sensor 352 monitors the ambient atmospheric pressure. The atmospheric pressure is used to compensate the other measured parameters for changes in atmospheric pressure.

Figure 18A:
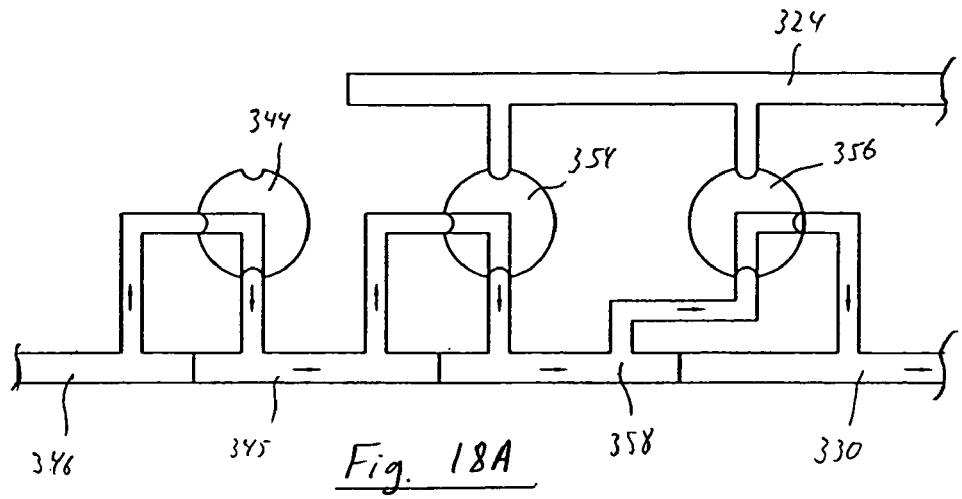
FIGS. 18A-18C illustrate the positions for the valve in the TGI flow control system of FIG. 17 to achieve the desired flow control.
Figure 18B:
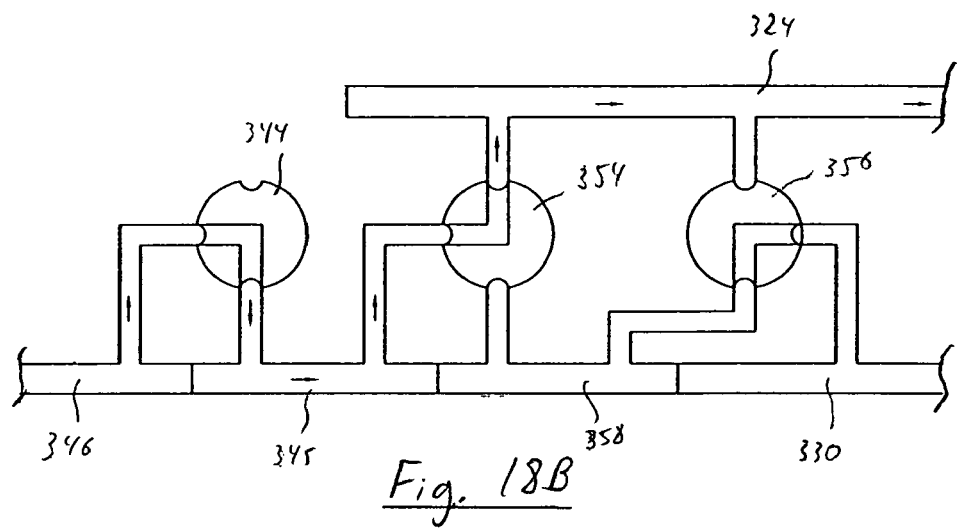
Figure 18C:
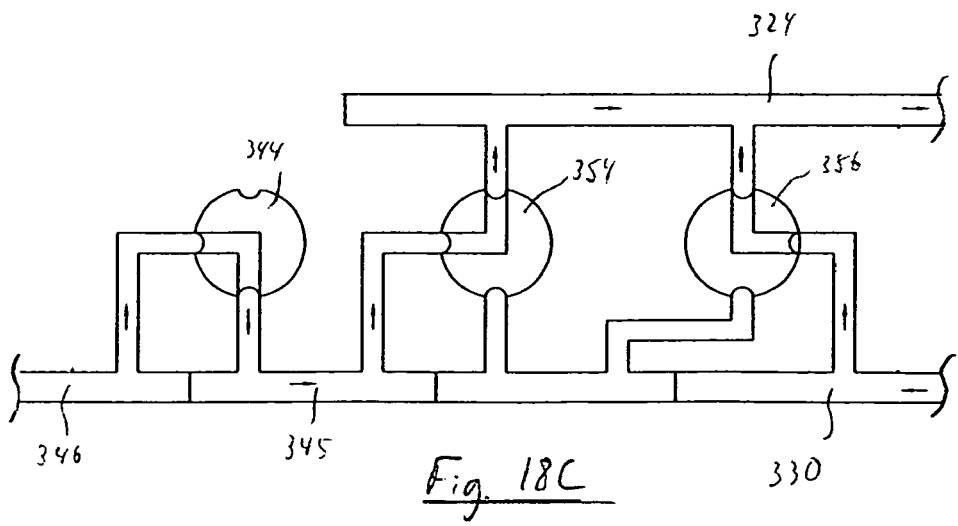

A bypass valve 354 and a vent valve 356 are provided in series between the source of insulation gas (the output of flow regulating valve 350), patient circuit via outlet line 324, and insulation catheter 322 via outlet line 330. Valves 354 and 356 are three-way valves that can be moved between two positions. The control of these valve is shown in FIGS. 18A-18C. Note that FIGS. 18A-18C do not show flow regulating valve 350.

In a TGI configuration shown in FIG. 18A, valves 354 and 356 communicate the insufflation catheter with the source of insufflation gas and disconnect the patient circuit from the source of insufflation gas and from the insulation catheter. This enables a flow of insufflation gas from the insufflation gas source to the insufflation catheter for delivery to the airway of the patient. More specifically, valve 354 is in an "enabled" position to communicate gas from line 345 to line 358 and disconnects all other flow paths. Valve 356 is also enabled to communicate gas from line 358 to line 330, and disconnects all other flow paths.

A "bypass" configuration for valves 354 and 356 is shown in FIG. 18B. This bypass configuration is needed when the user does not want a flow of insulation gas to be delivered to the insufflation catheter, but also does not want to disconnect the TGI system. This occurs, for example, where the caregiver desired to suction the patient to remove secretions. In this situation, there still is a continuous exhausting of gas from the TGI system as discussed above do the presence of exhaust valve 80 or 326. Therefore, there is still a need to input an equal amount of gas into the TGI system, but not into the insulation catheter. This is accomplished by providing the flow of insufflation gas, but bypassing it from the insufflation catheter. Instead, the flow of insufflation gas is delivered directly to patient circuit 306, where the constant flow exhaust assembly 326 is provided. In the bypass configuration, valve 354 is disabled, thereby communicating gas from line 345 to line 324 and disconnects all other flow paths. Valve 356 is enabled as noted above so that gas flows from the source of insufflation gas to the patient circuit and not to the TGI catheter.

Finally, a "vent" configuration for valves 354 and 356 is shown in FIG. 18C. This vent configuration allows the insufflation catheter to provide a path from the patient's lungs to the ambient atmosphere via the patient circuit. The source of insufflation gas is also prevented from being delivered to the insufflation catheter. In the vent configuration, valve 354 is disabled and valve 356 is also disabled to communicate line 330 with line 324 and disconnect all other flow paths.

The following table summarizes the position for bypass valve 354 and vent valve 354. Of course, the main shutoff valve 344 is enabled in these modes of gas delivery.

|             | Bypass Valve 354 | Vent Valve 356 |
| --- | --- | --- |
| TGI Mode    | Enabled          | Enabled        |
| Bypass Mode | Disabled         | Enabled        |
| Vent Mode   | Disabled         | Disabled       |

A pressure sensor 360 is provided at an outlet of valve 356 to monitor a pressure $P_{TGI}$ at the proximal end of the insufflation catheter. It is to be understood that pressure sensor 360 can be eliminated if not desired. An optional bacteria filter 362 is also provided at the outlet of the TGI flow control system. Finally, a housing 364 is provided to contain the elements of TGI flow control system 320.

Figure 19:
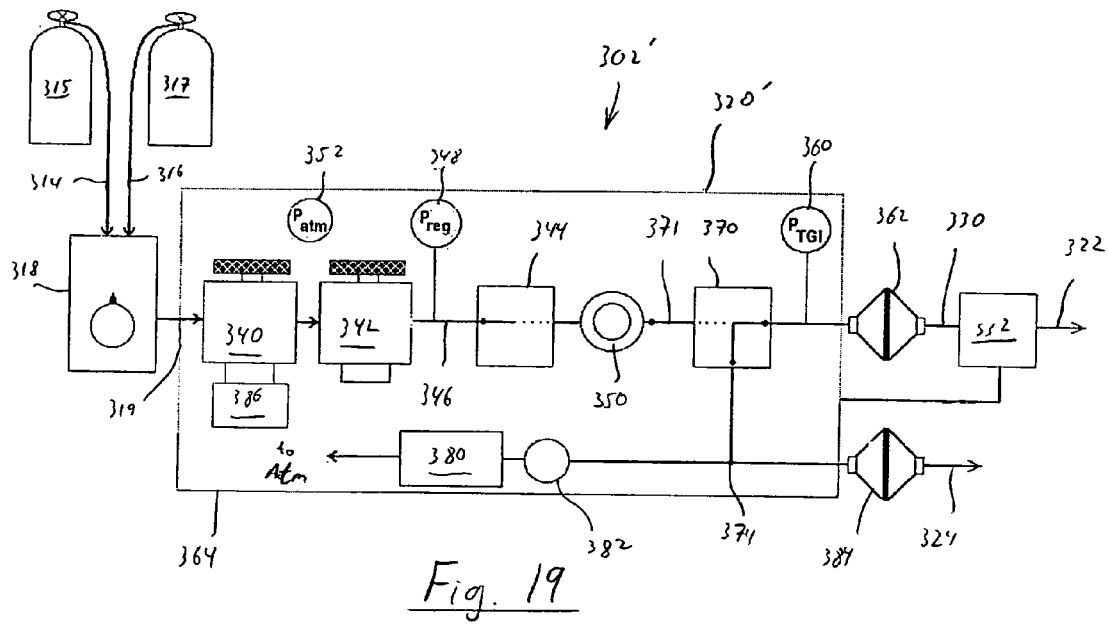
FIG. 19 is a schematic diagram of a second embodiment of a TGI flow control system according to the principles of the present invention.
Figure 20:
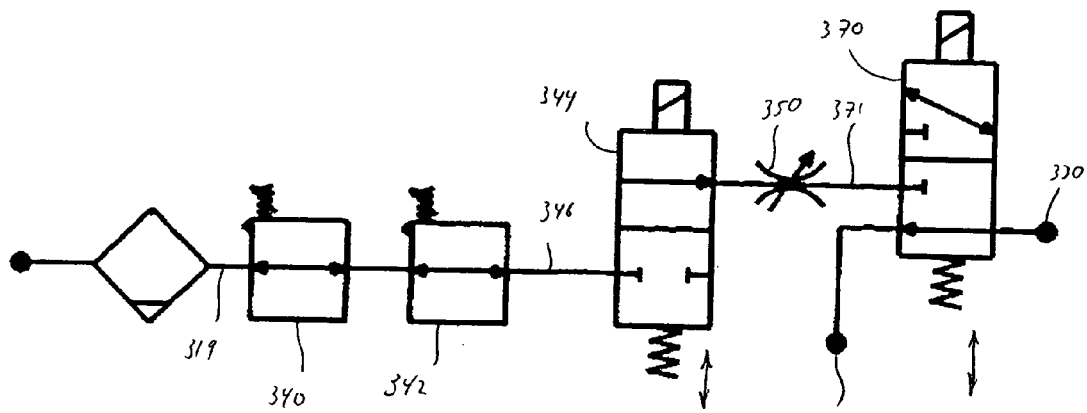
FIG. 20 is a flow schematic for the TGI flow control system of FIG. 19.

A second embodiment of a TGI flow control system 320' according to the principles of the present invention is shown in FIGS. 19 and 20, where FIG. 20 is a flow schematic for the TGI flow control scheme of FIG. 19. In this flow control technique, which is referred to as flow feedback control (FFC), the exhaust flow from the patient circuit is controlled by means of an active control feedback loop, rather than the through the use of a valve with a constant flow rate, such as valve 80 or 326. Thus, in this embodiment valve 326 is eliminated.

TGI flow control system 320' includes a single TGI/Vent valve 370 connected between the source of insufflation gas (an output 371 of needle valve 350), patient circuit via outlet line 324 and line 374, and insufflation catheter 322 via outlet line 330. Valve 370 is a three-way valve moveable between two positions. In a first "enabled" or TGI position, valve 370 communicates line 371 with line 330 so that the flow of insufflation gas is provided to the insufflation catheter. In this configuration, line 371 and line 330 are disconnected from line 374. In a second "disabled" or vent position, valve 370 communicates line 330 with line 374 so that the insufflation catheter is connected to the ambient atmosphere. In this configuration, line 371 is disconnected from lines 330 and 374.

In the FFC system 320', the constant exhaust flow that was otherwise provided by valve 326 is provided by a simple servo-controlled solenoid valve 380 and a flow meter 382. Valve 380 communicates the flow of gas from line 371 to ambient atmosphere. In a presently preferred embodiment, valve 380 is actively controlled based on the monitored flow via flow sensor 382 to provide a flow of exhaust gas from 0 to 15 liters per minute (lpm). Valve 380 is controlled so that the flow of exhaust gas substantially matches the flow insufflation gas so that there is no net increase in the volume of gas in the overall ventilation/TGI system over a respiratory cycle.

Valve 380 can be a bank of ON/OFF solenoid valves, an analog or digital (step motor) servo valve, a voice-coil valve, or any other valve that allows the flow rate to be controlled. In such a system, line 371 provides a pathway for gas from the exhalation limb of the patient circuit to valve 380 and flow meter 382. Valve 380 and 382 can be provided as separate elements of can be integrated into a single unit.

In this system, the patient circuit pressure provides the drive pressure across the valve 380. Thus, a minimum patient circuit pressure must be specified in order to use such a configuration. The system must be able to accommodate the saturated conditions of the gas. This could include removal of water from the gas prior to entry into valve 380 and/or flow meter 382, heating of measurement and control contact surfaces, or heating of the gas prior to entry into the measurement and control contact surfaces. A bacteria filter 384 is provided in line 324. In addition, a filter 386 is provided in the input line of the TGI flow control system.

It should be noted that the FFC system eliminates the need for a bypass flow control mode, because this system retains control of gas flow both into the and out of the patient circuit via valve 380. Nevertheless, a bypass mode can be provided by preventing a flow of insufflation gas from entering the insufflation catheter and preventing a flow of insufflation gas from entering the patient circuit.

The following table summarizes the position for main shutoff valve 344, TGI/Vent valve 370, and servo-controlled valve 380. It should be noted that in an enabled position, gas is allowed to flow in a controllable manner from line 374 to ambient atmosphere through valve 380 and in a disabled position the flow to ambient atmosphere through valve 380 is blocked.

|                | Shutoff Valve 344 | TGI/Vent Valve 370 | Exhaust Valve 380 |
| --- | --- | --- | --- |
| TGI Mode       | Enabled  | Enabled  | Enabled  |
| Bypass (1) Mode| Enabled  | Disabled | Disabled |
| Bypass (2) Mode| Disabled | Enabled  | Disabled |
| Vent Mode      | Disabled | Disabled | Disabled |

A further embodiment of the present invention contemplates using a roller pump in place of servo valve 380. Because a roller pump is a positive displacement device, volume flow is controlled simply by controlling the speed of the roller pump. Thus, a flow meter is not necessary because flow control could be executed via the pump motor speed. In a configuration with a roller pump, a tube that is connected to the patient circuit exhalation limb is wound around the inside of the pump mandrel. As the pump rollers rotate and compress the tubing, a given volume of gas is displaced from the patient circuit. An additional advantage to such a system is that there is no requirement for drive pressure from the patient circuit (i.e., no minimum patient circuit pressure).

Figure 21:
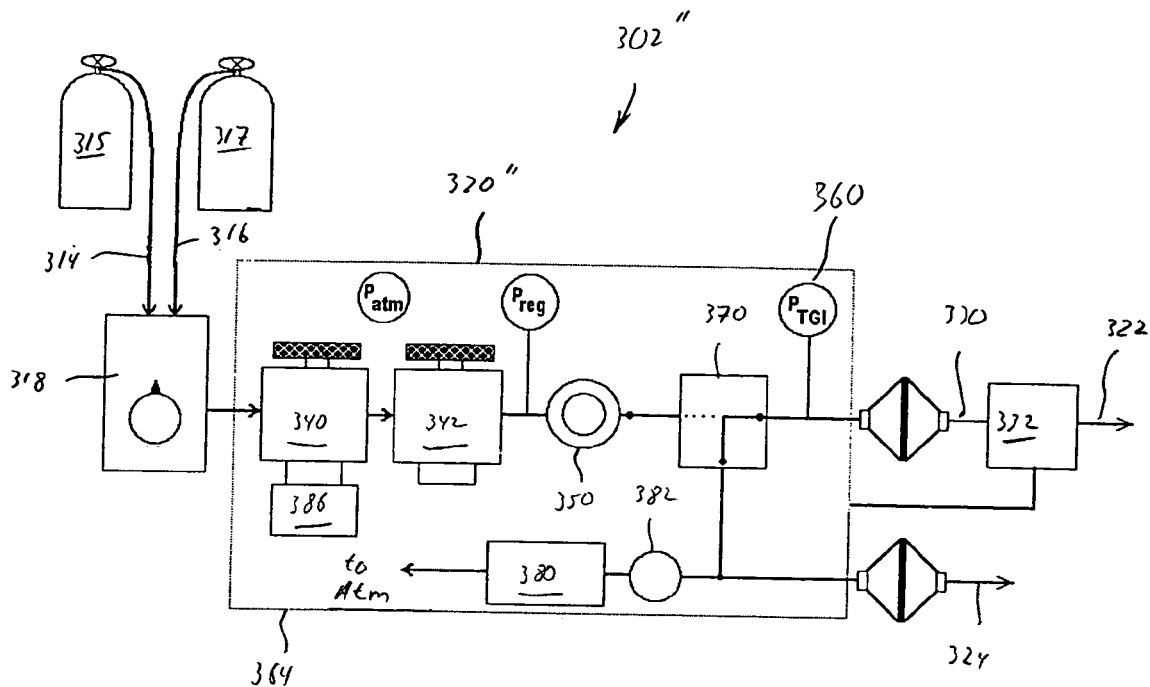
FIG. 21 is a schematic diagram of a third embodiment of a TGI flow control system according to the principles of the present invention.

FIG. 21 is a schematic diagram of a third embodiment of a TGI flow control system 320" according to the principles of the present invention. This embodiment is similar to that shown in FIG. 20, except that the main shutoff valve has been eliminated. The following table summarizes the position for TGI/Vent valve 370 and servo-controlled valve 380.

|             | TGI/Vent Valve 370 | Exhaust Valve 380 |
|---|---|---|
| TGI Mode    | Enabled  | Enabled  |
| Bypass Mode | Disabled | Disabled |
| Vent Mode   | Disabled | Disabled |

Figure 22:
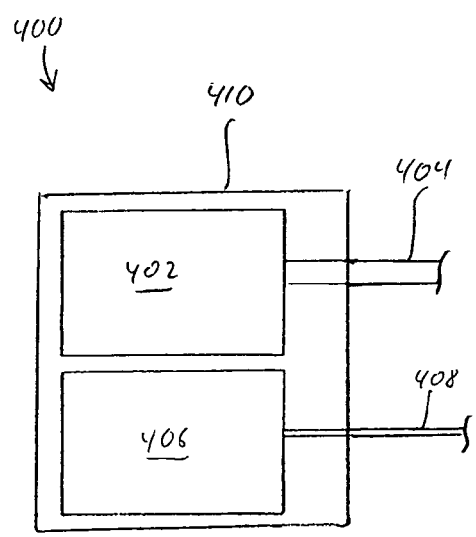
FIG. 22 is a schematic diagram of a first embodiment of a ventilator/TGI system combination according to the principles of the present invention.

In the embodiments discussed above, the ventilation system and the TGI system are shown as separate systems. However, the present invention also contemplates that these two systems can be incorporated into a single, integrated system. FIG. 22 is a schematic diagram of a first embodiment of a ventilator/TGI system combination 400 according to the principles of the present invention.

Ventilator/TGI system 400 includes a patient ventilation system 402 that generates a flow of gas for delivery to an airway of a patient. A patient circuit 404 is coupled to ventilation system 402 for carrying the flow of gas from the ventilation system to an airway of a patient. An insufflation system 406 provides a flow of insufflation gas for delivery to the patient's airway. An insufflation catheter 408 is coupled to the insufflation system for carrying the flow of gas from the insufflation system to an airway of a patient. A portion of the insufflation system is disposed within the patient circuit. A housing 410 contains both the patient ventilation system and the insufflation system.

Figure 23:
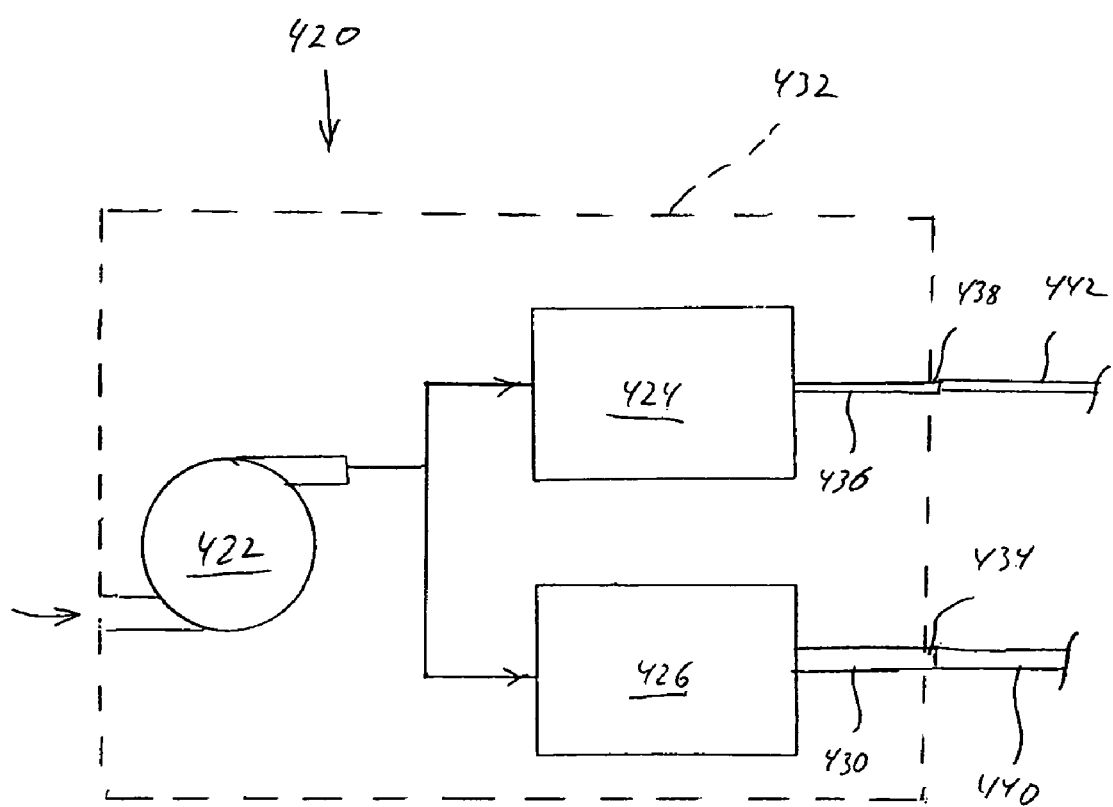
FIG. 23 is a schematic diagram of a second embodiment of a ventilator/TGI system combination according to the principles of the present invention.

The source of gas for the insufflation system and the ventilation system can be separate from one another. For example, in the previous embodiments, a pressure generator, such as a blower, piston, or bellows, creates the flow of gas for the ventilation system, and tanks of pressurized oxygen and air provide the insufflation gas. It is to be understood that these two sources of gas can be provided from a common source. For example, FIG. 23 illustrates a schematic diagram of a second embodiment of a ventilator/TGI system 420 combination according to the principles of the present invention. In this embodiment, a common pressure generator 422 generates a flow of pressurized gas for use by a TGI system 424 and a ventilation system 426. It is to be understood that a source of oxygen should be provided to the TGI system so that the flow of insufflation gas has an $FIO_2$ above that of air. The source of oxygen can be a tank of oxygen, an oxygen concentrator, a supply of liquid oxygen, or any other source of oxygen. It should also be understood that the supplemental oxygen can also be provided to the ventilation system, as is known in the art.

Referring again to FIG. 23, a first tube 430 is disposed in a housing 432 that connects an outlet of pressure generator 422 to a patient circuit connector 434. A second tube 436 also disposed in the housing connects a source of insufflation gas 422 to an insufflation catheter connector 438. A flow control system, which in the illustrated embodiment is ventilation system 426, is coupled to first tube 430 to control a flow of gas in a patient circuit 440 coupled to patient circuit connector 434. Another flow control system is coupled to second tube 436 to control a flow of insufflation gas to an insufflation catheter 442 coupled to insufflation catheter connector 438.

The present invention also contemplates providing the TGI flow control system discussed above with respect to FIGS. 17-21 in conjunction with the TGI/ventilation combined system. For example, the present invention contemplates providing one or move valves coupled between the first tube, the second tube, and the source of insufflation gas to control a flow of gas between the patient circuit, the insufflation catheter, and the source of insufflation gas as discussed above.

Pressure sensor 360 can be used to monitor the pressure at the lungs of the patient because the distal end portion of the insufflation catheter is disposed in the patient's lungs. The pressure $P_{TGI}$ measured at the proximal end of the insufflation catheter can be used to determine the pressure at the lungs if the pressure drop along the insufflation catheter is compensated. Of course, other environmental conditions and the dynamic compliance of the system should also be taken into consideration in order for the pressure measured by pressure sensor 360 to be an accurate determination of the pressure in the patient's lungs. This feature of the present invention allows pressure sensor 360 to be used to monitor the pressure in the patient's lungs. For example, it is important that the lung pressure does not exceed predetermined limits, which include a high pressure limit and a low pressure limit. Pressure sensor 360 can be used to monitor this pressure and provide alarms or shutoff decisions if the monitored pressure exceeds predetermined limits.

The present invention also contemplates controlling the $FIO_2$ of the gas provided by the ventilation system and/or controlling the $FIO_2$ of the gas provided by the TGI system so that the $FIO_2$ values of these gas flows are substantially the same. Matching the $FIO_2$ of the gas provided by the ventilation system and the $FIO_2$ of the gas provided by the TGI system can be accomplished manually, for example by having the user set the $FIO_2$ of the gas provided by the TGI system to match that of the ventilation system or vice versa.

Matching the $FIO_2$ of the gas provided by the ventilation system and the $FIO_2$ of the gas provided by the TGI system can also be accomplished automatically. For example, by monitoring the $FIO_2$ of the gas provided by the ventilation system using any conventional oxygen concentration monitoring system and automatically controlling the $FIO_2$ of the gas provided by the TGI system to match that of the ventilation system or vice versa. The $FIO_2$ matching between the TGI system and the ventilation system can also be provided by providing both systems with gas from the same source, i.e., having the same $FIO_2$.

A further embodiment of the present invention contemplates actively controlling the operation of the heated humidifier based on the monitored conditions of the ventilation system, the TGI system, or both. More specifically, the present invention contemplates causing the TGI flow control system to shut off the heat to the humidifier automatically if an alarm condition for the ventilation system, the TGI system, or both is detected. Typical alarm conditions that should cause the heat to be discontinued includes: high pressure, low pressure, and power supply errors. The present invention also contemplates decreasing or shutting off the heat to the heated humidifier when the flow of insufflation gas to the insufflation catheter is reduced or stopped. For example, if the insufflation flow is stopped so that a caregiver can suction the patient, the heat to the humidifier is also stopped. This prevents heating of the gas within the humidifier so that the patient does not receive a bolus of over-heated gas when the flow of insufflation gas to the insulation catheter resumes.

The present invention contemplates that the various components of the insufflation system of the present invention be made from any of a number of materials, so long as such materials are of sufficient strength and durability to function for their intended purpose. It is further desirable that, whenever necessary, the materials used for the various components of the present invention be compatible for use in medical applications.

Although the invention has been described in detail for the purpose of illustration based on what is currently considered to be the most practical and preferred embodiments, it is to be understood that such detail is solely for that purpose and that the invention is not limited to the disclosed embodiments, but on the contrary, is intended to cover modifications and equivalent arrangements that are within the spirit and scope of the appended claims.

What is claimed is:

1. A tracheal gas insufflation system comprising:
   a patient circuit adapted to couple a ventilator to an airway of a patient;
   an insufflation catheter having a proximal end portion located generally outside a patient and a distal end portion adapted to be located in an airway of a patient for providing a flow of insufflation gas to such a patient;
   a source of insufflation gas; and
   a flow control system coupled between the patient circuit, the insufflation catheter, and the source of insufflation gas so as to control a flow of gas between the patient circuit, the insufflation catheter, and the source of insufflation gas, wherein the flow control system includes a first selectively actuatable valve connected between the source of insufflation gas, the insufflation catheter, and the patient circuit, wherein the first valve is adapted to be arranged to:
   a) communicate the insufflation catheter with the source of insufflation gas and disconnect the patient circuit from the source of insufflation gas and the insufflation catheter in a first configuration,
   b) communicate the insufflation catheter with the patient circuit and disconnect the source of insufflation gas from the insufflation catheter and the patient circuit in a second configuration.

2. The system of claim 1, wherein the flow control system includes a servo-controlled valve adapted to control a flow of gas from the patient circuit to ambient atmosphere.

3. The system of claim 2, wherein the flow control system includes a flow sensor adapted to measure a flow of gas through the servo-controlled valve.

4. The system of claim 1, further comprising a master shut-off valve adapted to disconnect the source of insufflation gas from the insufflation catheter and the patient circuit.

5. The system of claim 1, further comprising a pressure sensor adapted to determine a pressure in the insufflation catheter.

6. A tracheal gas insufflation system comprising:
   a patient circuit adapted to couple a ventilator to an airway of a patient;
   an insufflation catheter having a proximal end portion located generally outside a patient and a distal end portion adapted to be located in an airway of a patient for providing a flow of insufflation gas to such a patient;
   a source of insufflation gas; and
   a flow control system coupled between the patient circuit, the insufflation catheter, and the source of insufflation gas so as to control a flow of gas between the patient circuit, the insufflation catheter, and the source of insufflation gas, wherein the flow control system includes a first selectively actuatable valve connected between the source of insufflation gas, the insufflation catheter, and the patient circuit, wherein the first valve is adapted to be arranged to:
   a) communicate the insufflation catheter with the source of insufflation gas and disconnect the patient circuit from the source of insufflation gas in a first configuration, or
   b) communicate the source of insufflation gas with the patient circuit and disconnect the insufflation catheter from the patient circuit and the source of insufflation gas in a second configuration.

7. The system of claim 6, further comprising a second selectively actuatable valve connected between the insufflation catheter and the patient circuit, wherein the second valve is adapted to communicate the insufflation catheter and the patient circuit responsive to the first valve being in the second configuration.

8. The system of claim 6, further comprising a master shut-off valve adapted to disconnect the source of insufflation gas from the insufflation catheter and the patient circuit.

9. A method of providing an insufflation gas to a patient comprising:
   providing a patient circuit adapted to couple a ventilator to an airway of a patient;
   providing an insufflation catheter having a proximal end portion located generally outside a patient and a distal end portion adapted to be located in an airway of a patient for providing a flow of insufflation gas to such a patient;
   providing a source of insufflation gas; and
   controlling a flow of gas between the patient circuit, the insufflation catheter, and the source of insufflation gas, wherein controlling the flow of gas between the patient circuit, the insufflation catheter, and the source of insufflation gas includes:
   a) communicating the insufflation catheter with the source of insufflation gas and disconnecting the patient circuit from the source of insufflation gas and the insufflation catheter in a first configuration,
   b) communicating the insufflation catheter with the patient circuit and disconnecting the source of insufflation gas from the insufflation catheter and the patient circuit in a second configuration.

10. The method of claim 9, further comprising controlling a flow of gas from the patient circuit to ambient atmosphere.

11. The method of claim 10, further comprising measuring a flow of gas through from the patient circuit to the ambient atmosphere.

12. The method of claim 9, further comprising disconnecting the source of insufflation gas from the insufflation catheter and the patient circuit via a master shut-off valve.

13. The method of claim 9, further comprising measuring a pressure in the insufflation catheter.

14. A ventilator and tracheal gas insufflation system comprising:
   a housing;
   a pressure generator disposed within the housing;
   a patient circuit connector disposed on an exterior of the housing adapted to connect to a patient circuit;
   an insufflation catheter connector disposed on the exterior of the housing adapted to connect to an insufflation catheter;
   a first tube disposed in the housing and connecting an outlet of the pressure generator to the patient circuit connector;
   a second tube disposed in the housing and connecting a source of insufflation gas to the insufflation catheter connector;
   a first flow control system operatively coupled to the first tube to control a flow of gas in the patient circuit; and a second flow control system operatively coupled to the second tube to control a flow of insufflation gas in the insufflation catheter.

15. The system of claim 14, wherein the second flow control system is coupled between the first tube, the second tube, and such a source of insufflation gas so as to control a flow of gas between the patient circuit, the insufflation catheter, and the source of insufflation gas.

16. The system of claim 14, wherein the source of insufflation gas is the pressure generator.

17. The system of claim 14, further comprising:

an insufflation catheter connected to the insufflation catheter connector; and a patient circuit connected to the patient circuit connector.

18. The system of claim 14, further comprising a sensor operatively coupled to the second tube to detect a characteristic associated with the flow of gas in the second tube.

* * * * *